(12) United States Patent
Takayanagi et al.

(10) Patent No.: US 9,447,191 B2
(45) Date of Patent: Sep. 20, 2016

(54) OSTEOGENESIS PROMOTER

(75) Inventors: Hiroshi Takayanagi, Tokyo (JP); Takako Negishi, Tokyo (JP)

(73) Assignee: National University Corporation Tokyo Medical and Dental University, Tokyo (JP)

(*) Notice: Subject to any disclaimer, the term of this patent is extended or adjusted under 35 U.S.C. 154(b) by 275 days.

(21) Appl. No.: 14/117,254

(22) PCT Filed: May 11, 2012

(86) PCT No.: PCT/JP2012/003113
§ 371 (c)(1),
(2), (4) Date: Jun. 25, 2014

(87) PCT Pub. No.: WO2012/157237
PCT Pub. Date: Nov. 22, 2012

(65) Prior Publication Data
US 2014/0303358 A1 Oct. 9, 2014

(30) Foreign Application Priority Data

May 13, 2011 (JP) ................................. 2011-108642

(51) Int. Cl.
*A61K 39/00* (2006.01)
*A61K 39/395* (2006.01)
*C07K 16/28* (2006.01)
*G01N 33/50* (2006.01)
*G01N 33/53* (2006.01)
*A61K 38/00* (2006.01)

(52) U.S. Cl.
CPC ........... *C07K 16/2896* (2013.01); *C07K 16/28* (2013.01); *C07K 16/2803* (2013.01); *G01N 33/5008* (2013.01); *G01N 33/53* (2013.01); *A61K 38/00* (2013.01); *A61K 2039/505* (2013.01); *G01N 2500/00* (2013.01); *G01N 2800/10* (2013.01)

(58) Field of Classification Search
None
See application file for complete search history.

(56) References Cited

U.S. PATENT DOCUMENTS

| | | | |
|---|---|---|---|
| 6,576,754 B2 | 6/2003 | Hall et al. |
| 7,700,102 B2 | 4/2010 | Hall et al. |
| 7,919,594 B2 | 4/2011 | Smith et al. |
| 8,067,247 B2 | 11/2011 | Belin et al. |
| 8,496,938 B2 | 7/2013 | Smith et al. |
| 8,816,058 B2 | 8/2014 | Smith et al. |
| 2006/0233793 A1 | 10/2006 | Belin et al. |
| 2008/0219971 A1 | 9/2008 | Smith et al. |
| 2010/0285036 A1 | 11/2010 | Smith et al. |
| 2012/0027758 A1 | 2/2012 | Belin et al. |
| 2012/0270268 A1 | 10/2012 | Smith et al. |
| 2013/0274449 A1 | 10/2013 | Smith et al. |
| 2014/0072578 A1 | 3/2014 | Smith et al. |

FOREIGN PATENT DOCUMENTS

| | | |
|---|---|---|
| JP | 2007-308465 | 11/2007 |
| JP | 2001-157583 A | 6/2012 |
| WO | 97/17368 A1 | 5/1997 |
| WO | 2004/067034 | 8/2004 |
| WO | 2010/129917 | 11/2010 |
| WO | 2008/100995 A1 | 8/2012 |

OTHER PUBLICATIONS

Negishi-Koga et al., Oct. 2011, Nature Medicine 17:1473-1481.*
Conrotto, P. et al., "Sema4D Induces Angiogenesis Through Met Recruitment by Plexin B1," Blood, vol. 105, No. 11, pp. 4321-4329 (2005).
Suzuki, K. et al., "Semaphorins and Their Receptors in Immune Cell Interactions," Nature Immunology, vol. 9, No. 1, pp. 17-23 (2008).
Roth, L. et al., "The Many Faces of Semaphorins: From Development to Pathology," Cellular and Molecular Life Sciences, vol. 66, No. 4, pp. 649-666 (2008).
Dacquin, R. et al., "Control of Bone Resorption by Semaphorin 4D Is Dependent on Ovarian Function," PLoS One, vol. 6, Issue 6, 11 pages (2011).
Ito, Y. et al., "Sema4D/Plexin-B1 Activates GSK-3β through R-Ras GAP Activity, Inducing Growth Cone Collapse," European Molecular Biology Organization, vol. 7, No, 7 pp. 704-709 (2006).
Dickinson, B.J., "Molecular Mechanisms of Axon Guide," Science, vol. 298, No. 5600, pp. 1959-1964 (2002).
Huber et al., "Signaling At the Growth Cone: Ligand-Receptor Complexes and the Control of Axon Growth and Guidance," Annual Review Neuroscience vol. 26, pp. 509-563 (2003).
Takagahara, "Plexin-A1 and its Interaction with DAP12 in Immune Responses and Bone Homeostasis," Nature Cell Biology, vol. 8, No. 6, pp. 615-622 (2006).
Zhao et al., "Biodirectional EphrinB-2-EphB4 Signaling Controls Bone Homeostasis," Cell Metabolism, pp. 111-121 (2006).
Oinuma et al., "The Semaphorin 4D Receptor Plexin-B1 Is a GTPase Activating Protein for R-Ras," Science, vol. 305, No. 5685, pp. 862-865 (2004).
Ishida et al., "Analysis of Physiological Action of Osteoclast-Derived Semaphorin 4D in Bone Metabolism," Meeting Program Abstracts of the Japan Society of Bone Metabolism vol. 25, p. 266, (2007).
Ishida et al., "Effect of Osteoclast-Derived Semaphorin 4D Against Osteblastic Function," Meeting Program Abstracts of the Japan Society of Bone Metabolism (2007).

(Continued)

*Primary Examiner* — Elizabeth C Kemmerer
(74) *Attorney, Agent, or Firm* — Thompson Coburn LLP

(57) ABSTRACT

The purpose of the present invention is to provide an osteogenesis promoter for directly promoting osteogenesis by osteoblasts, and an agent for preventing and treating bone disease. The present invention is characterized in that a binding inhibitor substance of semaphorin 4D and plexin B1 is used. For the binding inhibitor substance, suitable examples include anti-semaphorin 4D antibody, anti-plexin B1 antibody, and protein comprising the extracellular domain of plexin B1.

15 Claims, 29 Drawing Sheets

(56) References Cited

OTHER PUBLICATIONS

Dacquin et al., "Physiological Control of Bone Resorption by Semaphorin 4D is Dependent on Ovarian Function," ASBMR 2010 Annual Meeting Abstracts, Presentation Abstracts, Presentation No. MOO152.

Regev et al., "Semaphorin-4D (Sema-4D), The Plexin-B1 Ligand, is Involved in Mouse Ovary Follicular Development," Reproductive Biology and Endocrinology, vol. 5, No. 12, 8 pages (2007).

Oinuma et al., Semaphorin 4D/Plexin-B1-Mediated R-Ras GAP Activity Inhibits Cell Migration by Regulating β1 Integrin Activity, The Journal of Cell Biology, vol. 173, No. 4, pp. 601-613 (2006).

* cited by examiner

OSTEOGENESIS PROMOTER

CROSS-REFERENCE TO RELATED APPLICATIONS

The present application is the National Stage of International Application No. PCT/JP2012/003113, filed May 11, 2012, which claims priority to Japanese Application No. 2011-108642, filed May 13, 2011, each of which is incorporated herein by reference in its entirety.

REFERENCE TO A SEQUENCE LISTING SUBMITTED ELECTRONICALLY VIA EFS-WEB

This application includes a sequence listing ("1843_0730001_SequenceListing_ascii.txt", 39,601 bytes, created on Nov. 11, 2013) submitted electronically via EFS-Web, which is incorporated herein by reference in its entirety.

TECHNICAL FIELD

The present invention relates to an osteogenesis accelerator and to a preventive and therapeutic agent. It relates more particularly to an osteogenesis accelerator and to a preventive and therapeutic agent having as active ingredient a substance which inhibits binding of semaphorin 4D and plexin B1.

BACKGROUND OF INVENTION

As Japan's population ages, there has been an increase in patients suffering from bone fractures, osteoporosis, articular rheumatism, lumbar pain and other bone diseases. The function of tissue in bone tissue is maintained by coordinating osteoblasts which support osteogenesis and osteoclasts which support bone resorption and by maintaining a balance between osteogenesis and hone resorption. The balance of bone metabolism is destroyed by aging, a decline in ovarian function as well as other factors. When osteogenesis decreases or when there is abnormal bone resorption the bone quantity (bone density) decreases and a variety of bone diseases occur. Bone diseases include bone fractures, bone deficiency, osteoporosis, osteomalacia, osteopenia, lumbar pain, Paget's disease of bone, tonic myelitis, articular rheumatism, deformative arthrosis and the like. In particular, when an elderly person is afflicted with a bone disease, it is difficult for that person to function on a level required for daily life and depending on the case, there is a risk that the patient will become bed-ridden. As a result, this is extremely significant in the prevention and treatment of bone diseases in modern society where an increasing number of people are elderly.

Activated vitamin D3, biphosphonate, calcitonin, hormone preparations containing estradiol, vitamin K2 preparations and the like are generally used as therapeutic agents for bone diseases. Estradiol derivatives, activated vitamin D3 derivatives, biphosphonate derivatives and the like are being developed as more effective therapeutic agents as they have fewer side effects (see Patent Document 1). However, vitamin D3 has an action which increases the concentration of calcium in the blood and estradiol and biphosphonate have a bone resorption inhibition effect. However, none of these has an effect which directly accelerates osteogenesis through the osteoblasts. A multiple drug therapy is the treatment of choice in this case so that there is a need to develop a novel preventive and therapeutic agent having a different action from that of the conventional preventive and therapeutic agents.

Bones are being recreated continuously in stages known as bone remodeling wherein the bone resorption stage and the following osteogenesis stage are repeated. The transition from one stage to another must be controlled precisely by secretion from the bone cell as it contributes to the communication between the osteoclast-osteoblast or by bone reconstruction factors released from the bone matrix. It is well known that TGF-β and IGF-1 released during bone resorption stimulate osteogenesis so that it is known, as a coupling factor. Although there is an abundance of in vitro data on candidate molecules which are extremely important for the coupling factor, there is still no in vitro evidence for this.

Axon guidance molecules manifest widely outside the nervous system. Therefore, cell wandering, the immune response, tissue development and angiogenesis and the like are controlled (see Non-Patent Documents 1 and 2). Based on research carried out in recent years, it is suggested that the axon guidance molecules of semaphorin and ephrin and the like contribute to intercellular communication between osteoclasts and osteoblasts (see Non-Patent Documents 3 through 5).

It is well known that Semaphorin 4D is secreted from oligodentrocytes and that it induces destruction of the growth cone in the central nervous system. It is also clear that semaphorin 4D is extremely important in maintaining the immune response and the homeostasis of the immune system. One well-known semaphorin 4D receptor is plexin-B1 (see Non-Patent Document 6). Furthermore, Non-Patent Document 7 suggests that osteoclast formation can be accelerated through the osteoblast differentiation inhibition action as well as the osteoblasts. Non-Patent Document 8 discloses that semaphorin 4D is not detected in the osteoblasts, that it is present on the surface of the osteoclasts and the bone quantity has been confirmed to increase as compared to wild-type mice in female sema4D-/- mice where Semaphorin 4D (Sema 4D) is deficient in homo [zygotes].

PRIOR ART DOCUMENTS

Patent Documents

Special Table in Publication 2005-509629.
[Non-Patent Document 1] B. J. Dickson, Science 298, 1959 (Dec. 6, 2002)
[Non-Patent Document 2] A. B. Huber, A. L. Kolodkin, D. D. Ginty, J. F. Cloutier, Annual Review Neuroscience 26, 509 (2003)
[Non-Patent Document 3] N. Takagahara et al., Nat. Cell Biol 8, 615 (June, 2006)
[Non-Patent Document 4] N. Irie et al., Cell Metab 4, 111 (August, 2006)
[Non-Patent Document 5] C. Zhao et al., Cell Metab 4, 111 (August, 2006)
[Non-Patent Document 6] I. Oinuma et al., Science, Vol. 305, No. 5685, pp. 862-865 (Aug. 6, 2004)
[Non-Patent Document 7] Ishida Masanari, Kaneda Toshio, Muto Akihiro, Yoshida Masashi, Meeting Program Abstracts of the Japan Society of Bone Metabolism, vol. 25, page 266, published June 2007, [Analysis of Bioaction in Bone Metabolism in Osteoclast-derived Semaphorin 4D]
[Non-Patent Document 8] Romain Dacquin, Chantal Domenget, Pierre Jurdic, Irma Machuca-Gayet, ASBMR 2010 Annual Meeting Abstracts, Presentation Abstracts, Presentation Number MOO152, "Physiological Control of Bone Resorption by Semaphorin 4D is Dependent on Ovarian Function"

OVERVIEW OF INVENTION

Problems which the Present Invention is Intended to Solve

It is an object, of the present invention to provide an osteogenesis acceleration agent and a preventive and therapeutic agent, for bone diseases which involves direct promotion of osteogenesis using osteoblasts.

Means Used to Solve the Problems

After a great deal of hard work and research under the conditions described in the above-mentioned background of technology, the inventors found that (a) when semaphorin 4D which is derived from osteoclasts binds with the plexin B receptor on the osteoblast, it activates the small G protein RhoA which inhibits osteoblast differentiation, decreases the IRS signals (signals which promote the differentiation of the osteoblasts) and inhibit the differentiation of the osteoblasts so that osteogenesis is inhibited; and that (b) the anti-semaphorin 4D antibodies and anti-plexin B1 antibodies directly accelerate osteogenesis using the osteoblasts.

This means that the present invention relates to (1) an osteogenesis acceleration agent having as active ingredient a substance which inhibits binding between semaphoria 4D and plexin B1; (2) an osteogenesis acceleration agent as described in (1) above characteristic in that the binding inhibiting substance is an anti-semaphorin 4D antibody; and (3) an osteogenesis acceleration agent as described in (1) above characteristic in that the binding inhibiting substance is an anti-plexin B1 antibody or a protein containing plexin B1 extracellular regions.

The present invention also relates to (4) an agent for prevention and treatment of bone diseases having as active ingredient a substance winch inhibits binding of semaphorin 4D and plexin B1; (5) an agent for prevention and treatment of bone diseases as described in (4) above characteristic in that the binding inhibition substance is an anti-semaphorin 4D antibody; (6) an agent for prevention and treatment of bone diseases as described in (4) above characteristic in that the binding inhibition substance is an anti-plexin B1 antibody or a protein containing plexin B1 extracellular regions; and (7) an agent for prevention and treatment of bone diseases as described in any of (4) through (6) above characteristic in that the bone diseases are selected from bone fracture, bone deficiency, osteoporosis, osteomalacia, osteopenia, lumbar pain, Paget's disease of bone, tonic myelitis, articular rheumatism and deformative arthrosis.

The present invention also relates to (8) a method used to determine a candidate active ingredient for an osteogenesis acceleration agent wherein it is determined whether a substance being studied is a substance which inhibits binding between semaphorin 4D and plexin B1, and if the above-mentioned substance being studied is the abovementioned substance which inhibits binding, the abovementioned substance being studied is determined to be a candidate active ingredient for an osteogenesis acceleration agent; (9) a method as described in (8) above characteristic in that the method used to determine whether a substance being studied is a substance which inhibits binding between semaphorin 4D and plexin B1 consists of the following steps (A) through (D): (A) a step wherein semaphorin 4D and plexin B1 are brought in contact with one another in the presence of the substance being studied, (B) a step wherein the degree of binding between semaphorin 4D and plexin B1 is measured, (C) a step wherein the degree measured in step (B) above is compared with the degree when not in the presence of the substance being studied, and (D) a step wherein the substance being studied is determined to be a substance which inhibits binding between semaphorin 4D and plexin B1 when the degree measured in step (B) above is lower than the degree when not in the presence of the substance being studied; and (10) a method of screening for a candidate active ingredient for an osteogenesis acceleration agent characteristic in that, the methods described in (8) or (9) above are used to search substances being studied for a candidate active ingredient for an osteogenesis acceleration agent.

The present invention can be used to directly promote osteogenesis using osteoblasts and to prevent, and/or treat bone diseases.

BRIEF EXPLANATION OF FIGURES

FIG. 25 A diagram indicating results of studying the calcification formation of human osteoblasts (HOS) cultured in the presence of osteoclasts or the supernatant and/or the anti-Sema4D antibodies and the like.

PREFERRED MODE OF WORKING INVENTION

Figure 1:
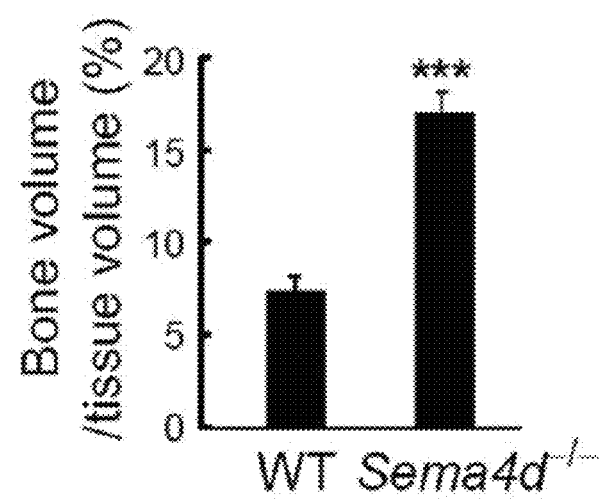
FIG. 1 A diagram indicating bone quantity in wild mice (WT) measured using microcomputer tomography ($\mu$CT) and semaphorin 4D knockout (Sema 4d-/-) mice.

There are no particular restrictions on the [osteogenesis accelerator] in the present invention and on the [preventive and therapeutic agent for bone diseases] (hereinafter referred to collectively as [agent in the present invention], as long as they have as active ingredient a substance which inhibits binding of semaphorin 4D and plexin B1 (hereinafter, referred to simply as [binding inhibiting substance in the present invention]) as the active ingredient and there are no particular restrictions on the binding inhibitor in the present invention as long as it is a substance which inhibits binding of semaphorin 4D and plexin B1 of vertebrates. However, protein comprising the extracellular regions of anti-semaphorin 4D antibodies, anti-plexin B1 antibodies, and plexin B1 can be cited as suitable examples. The binding inhibitor in the present invention inhibits binding of semaphorin 4D derived from osteoclasts and plexin B1 receptors on the osteoblasts and by inhibiting suppression, of differentiation of osteoblasts through RhoaA activation inhibition and through inhibition of lowering of IRS signals so that it is thought to accelerate osteogenesis using osteoblasts. Furthermore, in this Specification, the terms [inhibition] and [suppression] are used interchangeably.

The abovementioned anti-semaphorin 4D antibodies and anti-plexin B1 antibodies (hereinafter referred to as [antibodies in this invention]) may be polyclonal antibodies and may be monoclonal and any functional fragment of these. However, monoclonal antibodies are preferred given their high specificity. The abovementioned anti-semaphorin 4D antibodies and anti-plexin B1 antibodies may be produced using a conventional well-known method using semaphorin 4D and plexin B1. The functional fragments which, are the antibodies in the present, invention indicate fragments of antibodies which bind specifically relative to (a) semaphorin 4D which is an antigen in which the antibodies in the present invention bind specifically and to (b) plexin B. Specific examples are F (ab') 2, Fab', Fab, Fv, disulphide-linked FV, single-chain FV (scFV) and polymers of these (D. J. King, Applications and Engineering of Monoclonal Antibodies, 1998 T. J. International Ltd.). These antibody fragments can be obtained, by using a conventional method such as digestion of antibodies molecules using papain, pepsin and other proteases or by using a well-known genetic engineering method.

The antibodies in the present invention also include human antibodies. Here, [human antibodies] as these relate to the present invention indicate antibodies which are manifested products of human-derived antibody genes. Human antibodies can be obtained by introducing a human antibody gene locus and administering semaphorin 4D and plexin B1 in transgenic animals which are capable of producing human-derived antibodies. A mouse is an example of said transgenic animal. Mice which are capable of producing human antibodies, for example, are deficient in endogenous mouse immunoglobulin (Ig) heavy chains and mouse κ light chains and mice can be used which simultaneously retain a 14th chromosome fragment (SC20) comprising the human Ig heavy chain genes as well as human $Ig_k$ chair, transgenes (KCo5). These mice are produced by breeding strain A mice having a human Ig heavy chain gene locus and strain B mice having a human $Ig_k$ chain transgene. The strain A mice are homozygotes for both endogenous Ig heavy chain and $_k$ light chain destruction and they are a mouse strain (Tomizuka, et al., Proc Natl Acad Sci USA, 200 Vol 97:722) which retain a 14th chromosome fragment (SC20) which is capable of apomorphic transmission. Strain B is also a homozygote for both endogenous mouse Ig heavy chains and $_k$ light chain deficiency and is a mouse strain (Nat Biotechnol., 1996 Vol 14:845) which retains a human $Ig_K$ chain transgene (KCo5).

The polyclonal antibodies in the present invention may be produced using the method indicated below. They can be obtained by using semaphorin 4D and plexin B1 and if necessary an immunoactivation agent (Freund's adjuvant and the like) on mice, rabbits, goats, horses and other non-human mammalians. The monoclonal antibodies in the present invention are used to produce hybridoma from antibody producing cells from immunosensitized animals and myeloma cells which cannot produce their own antibodies. The hybridoma is cloned and clones are selected which produce monoclonal antibodies indicating specific affinity toward the antigens used for immunization. Said hybridoma can be produced based on the method of Keller and Millstein (Nature, 1975 Vol. 256:495-497). Screening of the hybridoma clone which produces monoclonal antibodies is carried out by culturing the hybridoma in a micro-titer plate. The responsiveness to the immunoantigens in the culturing supernatant in the wells seen to have proliferated can be carried out by measuring using ELISA and other enzyme immunoassay methods, radioimmunoassay, the fluorescent antibody method and other immunological methods.

Producing monoclonal antibodies from hybridomas can be carried out by culturing the hybridoma in vitro and isolating it from the supernatant. It can also be cultured in vivo in the pleural fluid of mice, rats, guinea pigs, hamsters or rabbits and the like and isolated from the pleural fluid. The genes which code monoclonal antibodies from hybridoma and other antibody producing cells are cloned, recombined in a suitable vector and these are introduced in the host (for example, Chinese hamster ovary (CHO) cells and other mammalian cell stock, *Escherichia coli*, yeast cells, insect cells, plant cells and the like) and the recombinant antibodies are produced using gene recombination technology (P. J. Delves, Antibody Production Essential Techniques, 1997, Wiley, P. Shepherd and C. Dean, Monoclonal Antibodies, 2000, Oxford University Press. J. W. Coding, Monoclonal Antibodies: Principles and Practice, 1993, Academic Press).

Transgenic cows, goats, sheep or pigs wherein me desired antibody genes which are recombined in endogenous genes using transgenic animal production technology are produced and large quantities of antibodies derived from antibody genes are obtained from the milk of these transgenic animals.

The antibodies produced can be refined using a well-known method in the field such as a combination of protein A column chromatography, ion exchanged chromatography, hydrophobic chromatography, the sulfate analytical, method, gel filtration, affinity chromatography and the like.

The protein comprising the extracellular region of the abovementioned plexin B1 can inhibit binding of semaphorin 4D and plexin B1 by trapping semaphorin 4D. There are no particular restrictions on the protein which comprises the plexin B1 extracellular region, however, a protein which fuses with the constant region of the antibodies (preferably any immunoglobulin Fc fragment) is a suitable example.

The protein which comprises the abovementioned semaphorin 4D, plexin B1 and plexin B1 extracellular regions can produce a manifestation vector which comprises that sequence based on the sequence information of these proteins. The manifestation vector is subjected to phenotypic transformation in suitable host cells, the target protein is produced inside the cells and the target protein can be introduced by using an isolating method or other well-known method. For example, the DNA sequences (sequence number 1) of human semaphorin 4D and the amino acid sequence (sequence number 2) are disclosed in GenBank Accession Number NM_0011422.87 and the DNA sequence (sequence number 3) of human plexin B1 and the amino acid sequence (sequence number 4) are disclosed in GenBank Accession Number NM_001130082. Furthermore, the human plexin B1 extracellular region corresponds to amino acid numbers 1 through 1490 of the amino acid sequence of the abovementioned Accession Number NM_001130082.

We measured by immunoblotting analysis the binding between semaphorin 4D and plexin B1 both in the presence of and not in the presence of the substance to see whether a certain, substance is a substance which inhibits binding of semaphorin 4D and plexin B1 and studied whether the bond between them decreased in the presence of that substance so that it could be easily confirmed.

The osteogenesis acceleration effect referred to in the present invention indicates the effect, of accelerating osteogenesis and more precisely includes the effect of accelerating osteogenesis by osteoblasts by inhibiting the suppression of differentiation of osteoblasts. Whether or not a certain substance has an osteogenesis acceleration effect can be confirmed by administering the substance to vertebrates having a lower bone quantity than usual (preferably patients with osteoporosis and osteoporosis model vertebrates) and finding whether or not the bone quantity increases.

The bone disease prevention and treatment effect in the present invention indicates the effect of preventing and/or treating any of the bone diseases or the effect of improving the symptoms in the present invention. Whether or not a certain substance has a bone disease therapeutic effect can be confirmed by administering the substance to a patient or a vertebrate with a bone disease (preferably a patient with osteoporosis or an osteoporosis model vertebrate) and then studying whether the bone disease is cured or improved.

The formulation of the present invention may contain only the binding inhibition substance in the present invention, however, a usually pharmacologically permitted carrier, binding agent, stabilizer, excipient, diluent, pH buffer, disintegrator, solubilizing agent, solubilization adjuvant, isotoner and other adjustment agent compounding components may be added. The formulation of the reducing agent in the present invention may be a powder formulation, granulated formulation, a capsule agent or other solid preparation. It may also be a solution preparation, an emulsion, a suspension or other liquid formulation. These preparations may be used as suitable for the binding inhibition substance in the present invention by treating using the regular method.

There are no particular restrictions on the method used to administer the agent in the present invention as long as it has the desired bone disease preventive or therapeutic effect and it may be administered orally or non-orally. The non-oral method used to administer it includes vascular administration, muscular administration, hypodermic administration, transdermal administration, nasal administration, transpulmonary administration. Of these, vascular and intravenous administration can be used to particular advantage. The dose of the preparation in the present invention as well as the number of times administered and the concentration can be adjusted in accordance with the body weight of the subject, the type of bone disease and the bone disease symptoms.

The subject for the present invention may be vertebrates such as mammalians and animals belonging to the bird family. These may include humans, monkeys, mice, rats, hamsters, guinea, pigs, cows, pigs, horses, rabbits, sheep, goats, cats, dogs, chickens, quail and other suitable animals. Of these, humans and domestic animals and fowl are particularly suitable. The binding inhibiting substance contained in the agent of the present invention is suitable from the standpoint of obtaining an outstanding osteogenesis acceleration effect and the bone disease prevention and treatment effect whether the type of vertebrate derived from semaphorin 4D and plexin B1 which bring out the binding inhibition action coincides with the type of vertebrate which is a candidate for administration of the agent in the present invention. Furthermore, a vertebrate derived from semaphorin 4D and the type of vertebrate derived from plexin B1 may be the same or different.

There are no particular restrictions on the type of bone disease which can be treated using the present invention as long as it is a bone disease having a factor which brings about a decline in osteogenesis or a bone disease related to a decline in osteogenesis. However, bone fractures, bone deficiency, osteoporosis, osteomalacia, bone deficiency, lumbar pain, Paget's disease of bone, tonic myelitis, articular rheumatism, dysosteogenesis and deformative arthrosis are all suitable candidates. Of these, osteoporosis, osteomalacia, osteopenia and dysosteogenesis are particularly suitable.

The method in the present invention is a method used to determine a candidate active ingredient for an osteogenesis acceleration agent wherein it is determined whether a substance being studied is a substance which inhibits binding between semaphorin 4D and plexin B1, and if the abovementioned substance being studied is the abovementioned substance which Inhibits binding, the abovementioned substance being studied is determined to be a candidate active ingredient for an osteogenesis acceleration agent, in the abovementioned determination method, the following steps (A) through (D) are a suitable example of the method used to determine whether a substance being studied is a substance which inhibits binding between semaphorin 4D and plexin B1:

(A) a step wherein semaphorin 4D and plexin B1 are brought in contact with one another in the presence of the substance being studied;

(B) a step wherein the degree of binding between semaphorin 4D and plexin B1 is measured;

(C) a step wherein the degree measured in step (B) above is compared with the degree when not in the presence of the substance being studied;

(D) a step wherein the substance being studied is determined to be a substance which inhibits binding between semaphorin 4D and plexin B1 when the degree measured in step (B) above is lower than the degree when not in the presence of the substance being studied.

In the abovementioned determination method, the following may be used to measure the degree of binding: for semaphorin 4D, labeled semaphorin 4D extracellular region or fusion protein of semaphorin 4D extracellular region and immunoglobulin Fc region, etc., and for plexin B1, a cell expressing plexin B1 on its surface. The following may also be used to measure the degree of binding: for plexin B1, labeled plexin B1 extracellular region or fusion protein of plexin B1 extracellular region and immunoglobulin Fc region, etc., and for semaphorin 4D, a cell expressing semaphorin 4D on its surface.

There are no particular restrictions on the substance being studied in the determination method in the present invention and it may be a substance predetermined to have an activity which inhibits binding of semaphorin 4D and plexin B1 and it may be any substance whose activity is unknown. It is also possible to simultaneously use multiple substances being studied. When simultaneously using multiple substances being studied, it is possible to simultaneously use individual substances being studied each in a separate sample, to simultaneously use multiple substances being studied in a single sample, or to simultaneously use multiple samples individually prepared with multiple substances being studied. When simultaneously using multiple substances being studied in a single sample, it may not be possible in one test to determine which of the substances being studied inhibits binding of semaphorin 4D and plexin B1, but it is possible to determine which of the substances being studied is a binding inhibitor by running the test multiple times and narrowing, down the substances being studied in stages. The determination method in the present invention is characterized by searching substances being studied for a candidate active ingredient for an osteogenesis acceleration agent, and the method can be used to screen for a candidate active ingredient for an osteogenesis acceleration agent.

Furthermore, other modes of the present invention may involve (a) use of the binding inhibition substance in the present invention in the production of the preventive and therapeutic agent for the abovementioned osteogenesis acceleration agent and bone diseases; (b) a binding inhibition substance in the present invention for use as an osteogenesis acceleration agent and in the prevention and treatment of bone diseases; (c) a method of using the binding inhibition substance for the acceleration of osteogenesis and prevention and treatment of bone diseases; (d) a method of promoting osteogenesis by administering the binding inhibition substance in the present invention; and (e) a method of preventing and treating bone diseases by administering the binding inhibition substance in the present invention.

Next we shall describe the present invention in detail referring to practical examples of it, however, it should by no means be construed that the present invention is restricted to these practical examples.

Practical Examples 1

[Analysis of Mice and Bone Phenotypes]

We produced the Sema4d-/-, Plxnb1-/-, plexin B2 knockout (Plxnb2-/-), CAT-RhoA DN and α 1 (1)-Cre mice in accordance with the method described in the literature (W. Shi et al., Immunity 13, 633 (November, 2000); R. H. Friedel et al., J Neurosci 27, 3921 (Apr. 4, 2007); R. H. Friedel et al., Proc Natl Acad Sci USA 102, 13188 (Sep. 13, 2006); K. Kobayashi et al., J. Neurosci 24, 3480 (Apr. 7, 2004); R. Dacquin, M. Starbuck, T. Schinke; G. Karsenty, Dev Dyn 224, 245 (June, 2002)]. All of the mice were backcrossed 8 or more times with C57BL/6 mice. All of the mice were maintained in a condition where there was no specific pathogenic fungus. All of the animal experiments were authorized by the Animal Experiment Committee of the Tokyo Medical and Denial University and complied with related guidelines and laws. Analysis of the bone phenotype involved controlling respectively the genetically altered mice and the mice for a the same litter and we analyzed at least 8 males and 8 females. Three-dimensional micro CT (μCT) analysis and histomorphological measurement analysis were carried out in accordance with the methods described, in the literature (K. Nishikawa et al., J Clin Invest 120, 3455 (Oct. 1, 2010); T. Koga et al., Nature 428, 758 (Apr. 15, 2004).

[Bone Marrow Chimera Mice]

We produced bone marrow chimera mice by changing in part the method described in the literature (B. Zhao et al., Nat Med 15, 1066 (September, 2009). This means that we collected donor bone marrow cells (C57BL6-Ly5, 2 backgrounds) from wild-type Sema 4d-/- mice from the same litter. We injected intravenously 2×106 cells obtained from each donor in the caudal vein of wild type recipient mice (3 weeks old, C57BL/6-Ly5, 1 background) exposed to lethal radiation or Sema4d-/- mice. Eight weeks after bone marrow transplant, a high level donor type chimerism (>95%) was attained.

[GeneChip Analysis]

We carried out GeneChip analysis in accordance with the method described in the literature (K. Nishikawa et al., J Clin Invest 120, 3455 (Oct. 1, 2010)). This means that after cDNA synthesis was carried out using reverse transcription using all of the RNA, we synthesized the cRNA which had been subjected to biotinized labeling by transcription in vitro. After we fragmented, the cRNA, we carried out hybridization using the mouse A430 GeneChip (made by Affymetrix) in accordance with the method described in the literature (T. Koga et al., Nat Med 11, 880 (August, 2005); H. Takayanagi et al., Dev Cell 3, 889 (December, 2002).

[Induction of Differentiation to Osteoblasts In Vitro]

Induction of differentiation to osteoblasts and osteoclasts in vitro was carried out according to the method described in the document (T. Koga et al., Nat Med II, 880 (August, 2005); and H. Takayanagi et al., Dev Cell 3, 889 (December, 2002). This means that we carried out differentiation induction by carrying out culturing of calvaria-derived cells in an osteogenesis culture medium (50 μM of ascorbic acid 10 nM of dextrasone, and 10 mM of β glycerophosphate) and the differentiation induction was confirmed by alkaline phosphatase (ALP) assay (after 7 days) and osteonodosity analysis (21 days later, alizarin red staining). Fc-sema4D, anti-Semar4D antibodies and anti-plexin BA antibodies (anti-Plexin-B1 antibodies) was added every 3 days. The osteoclast supernatant was recovered from each of the culture solutions of the wild type and Sema4d-/- cells after stimulating the intranuclear factor κ B activated receptor ligand (RANKL; made by Peproteeh). We cultured the cultured osteoclasts in a collagen code dish (made by IWAKI) and recovered it using trypsin two days after RANKL stimulation. The osteoclast supernatant was used as an osteogenesis culture medium containing the abovementioned reagent and we added it to the cultured osteoclasts (1×150 cell/well, 24 well-plate) every 3 days.

[Quantitative Real-Time RT-PCR Analysis]

Quantitative real-time RR-PCR was carried out in accordance with the product protocols using a light cycler device (made by Roche) and SYBR Green (made by Toyobo). We used the following primers.

```
Plxnb1 sense:
                            (sequence number 5)
5'-tgggtcatgtgcagtacgat-3', Plxnb1 antisense:
                            (sequence number 6)
5'-cactgctctccaggttctcc-3', Plxnb2 sense:
                            (sequence number 7)
5'-aggggagcctctctacaagc-3', Plxnb2 antisense :
                            (sequence number 8)
5'tcgatcccttcatcctgaac-3', Plnxb3 sense:
                            (sequence number 9)
5'-atatgctgagcgtgccttct-3', Plnxb3 antisense:
                            (sequence number 10)
5'tgctgttgagcaaattggag-3', CD72 sense:
                            (sequence number 11)
5'-gccttctcctgtcctgtctg-3', CD72 antisense:
                            (sequence number 12)
5'-cctcctggaactgctgagac-3', Alpl sense:
                            (sequence number 13)
5'-aacccagacacaagcattcc-3'

Alpl antisense:
                            (sequence number 14)
5'-gcctttgaggtttttggtca-3'

Bglap sense:
                            (sequence number 15)
5'-gcgctctgtctctctgacct-3', Bglap antisense:
                            (sequence number 16)
5'-accttattgccctcctgctt-3', Col1a1 sense:
                            (sequence number 17)
5'gagcggagagtactggatcg-3', Col1l1 antisense:
                            (sequence number 18)
5'-gttcgggctgatgtaccagt-3'

Gapdh sense:
                            (sequence number 19)
5'-acccagaaagactgtggatgg-3',
```

[Genetic Introduction of Adenovirus and Retrovirus]

The method of producing the adenovirus vector carrying the configuration active type (CA) of RhoA (Myc-V14Rho) and Rac1 (hRac1 V12) and the dominant negative type (DN) of the RhoA (Myc-N19Rho) and Rac1 (hRac1 V12) and the method of introducing these were carried out in accordance with the method described in the literature (Bito, H. et al., A Critical Role for a Rho-Associated Kinase, p160ROCK, in Determining Axon Outgrowth in Mammalian CNS Neurons, Neuron 26, 431-441 (2000). Producing the retrovirus vector (pMXs-Plexin-B1-EGFP, pMXs-Plexin-B1 RA-EGFP and pMXs-Plexin-B1 DPDS-EGFP where the mutant [Plexin-B1 DPDZ-EGFP]) manifested wherein activation of [Plexin-B1 RA] and RhoA could not be activated was carried out by inserting the cDNA fragment, of respectively Plexin-B1, Plexin-B1 RA (L Oinuma, Y. Ishikawa, H. Katoh, M. Negishi, Science 305, 862 (Aug. 6, 2004) and Plexin-B1 DPDZ (V. Perrot, J. Vazquez-Prado, J. S. Gutkind, J Biol Chem 277, 43115 (Nov. 8, 2002)) in pMXs-IRES-EGFP. Production of a recombinant retrovirus was carried out in accordance with the method described in the literature (S. Morita, T. Kojima, T. Kitamura, Gene Ther 7, 1063 (June, 2000). This means that we carried out a retrovirus packaging by introducing the retrovirus vector produced in the Plat-E cells.

[Anti-Sema4D Anti-Body Processing for OVX Induced Decline in Bone Quantity]

Producing osteoporosis model mice induced by OVX (ovaries extracted) was carried out in accordance with the method described in the literature (M. Shinohara et ah, J. Bio Chem 282, 17640 (Jun. 15, 2007). This means that we carried out an ovarian extraction operation or pseudo operation on 7 week old female mice. Of these model mice, we carried out tests on more than 6 mice in each group. We validated this using the method indicated below to find out whether or not there was a preventive effect on the decline in bone quantity. This means that we injected intravenously 20 µg of Sema4D antibodies (made by MBL) or a saline solution from the caudal vein once a week. We sacrificed all of the mice 8 weeks after surgery and carried out µCT analysis and osteomorphogenesis analysis. We also carried out validation using the following method to study whether or nor there was an acceleration effect on the bone quantity which had decreased. This means that after 6 weeks we injected intravenously 20 µg of anti-Sema4D antibodies (made by MBL) from the caudal vein for 3 weeks every 3 days in OVX mice. We sacrificed all of the mice 9 weeks after the operation and used them for µCT analysis.

[Immunoblotting Analysis, Pull Down Analysis and Immunofluorescent Staining]

We cultured calvarial cells for two days in an osteogenesis culture medium (50 µM of ascorbic acid, 10 nM of dexamethasone and 10 mM of β-glycerophosphate) and then stimulated these with Fc-Sema4D. We used purified human IgG (Fc part) (made by Beckman Coulter) for native control for pull down analysis (time 0). We collected cells at the point indicated and carried out immunoblotting analysis or pull down analysis using anti-Plexin-B 1 antibodies (clone A-8, made by Santa Cruz); anti-PDZ-RboGEF antibodies (polyclonal, made by Protein Express); anti-LARG antibodies (polyclonal, made by Lifespan Biosciences); anti-phospho-Akt antibodies (Thr308) (polyclonal, made by Cell Signaling); anti-Akt antibodies (polyclonal, made by Cell Signaling); anti-phosphor ERK antibodies (Thr202/Tyr204) (polyclonal, made by Cell Signaling); anti-ERK antibodies (polyclonal, made by Cell Signaling); anti-Met antibodies (clone 25H2) (made by Cell Signaling); anti-ErbB2 antibodies (clone 29D8) (made by Cell Signaling); anti-Rac1 antibodies (clone 102/Rac1) (made by BD Transduction Laboratories); anti-RhoA antibodies (clone 55/Rho) (made by BD Transduction Laboratories); anti-cadherin-11 antibodies (polyclonal, made by Invitrogen); anti-IRS1 antibodies (clone 53-10C-31) (made by Millipore); and anti-b-actin antibodies (clone AC40) (made by Sigma-Aldrich). The phosphorylation of plexin B1, Met, ErbB2 and IRS1 was detected by anti-phosphotyrosine antibodies (4G10, made by Upstate) after immunoprecipitation using respectively specific antibodies for these. We incubated a cell dissolved product with Fc-sema4D (500 ng) which binded with protein A-agarose beads in order to detect the plexin B1 which binded to semaphorin 4D and carried out immunoblotting analysis using anti-Plexin-B1 antibodies. Detecting activation of the GTPase was carried out in accordance with the description in the literature (M. Shinohara et al., J Bio Chem 282, 17640 (Jun. 15, 2007). This means that we treated the calvarial cells with Fc-sema4D and collected them at the point they were displayed. We incubated the cell dissolved product with GST-RBD (using RhoA) or GST-PAK1 (using Rac1) (2 µg) which binded with glutathione sepharose and we carried out immunoblotting analysis using respectively anti-RhoA antibodies or anti-Rac1 antibodies. We fixed the cells with a 4% paraform aldehyde for immunofluorescent staining, carried out permeation processing and then stained it using Alex Fluor 488 labeling secondary antibodies and rhodamine conjugate phalloidin (made by Molecular Probes).

[Flow Cytometry]

We stained a single cell floating solution using monoclonal antibodies conjugated with 8 types of fluorescent pigments [anti-CD45. 2 antibodies conjugated with Per-CP.Cy5.5; anti-CD45.2 antibodies (clone 104) conjugated with FITC; anti-CD11b antibodies (clone M1/70) conjugated with eFLuor450; anti-CD105 antibodies (clone MJ7/18) conjugated with PE; anti-CD10 antibodies (clone 4.29E+02) conjugated with Alex Fluor 647; (anti-CD44 antibodies conjugated with APC-Alexa Fluor 750; anti-Cd 44 antibodies (clone IM7) conjugated with AC-Cy7; and anti-Sca-1 antibodies (clone D7) (made by eBioscience) conjugated with APC in order to analyze the bone marrow derived cells and the calvarial cells. Then, we carried out flow cytometry using FACSCant II using Diva software (made by BD Biosciences).

[Cell Proliferation Analysis]

We cultured bone marrow-derived interstitial cells in an osteogenesis condition culture medium and analyzed the cell proliferation rate before osteoblast differentiation (Day 0) or in the osteoblast differentiation process (Day 14) using semaphorin4D stimulation using human IgG Fc partial or using cell proliferation ELISA kit (made by Roche) in the presence of Fc-Semar4D and detected the incorporation of 5-bromo-2' deoxyuridine (BrdU).

[Analysis of Colony Formation Unit (CFU)]

We plated the bone marrow cells at $3 \times 10^6$ cells per single well on a 24-well plate. Then, we cultured this for 3 days using α-MEM culture medium containing 10% fetal calf serum and then replaced it with an osteogenesis condition culture medium. The colony formation unit-alkali phosphatase (CFU-ALP) was detected as an ALP positive colony on the $7^{th}$ day and the CFU-osteoblast (CFU-Ob) was detected as an alizarin red positive colony on day 21. The aggregate number of colonies (CFU-fibroblasts (CFU-F)) was detected by staining with toluidine blue on day 7 and day 21.

[Statistical Analysis]

All of the data are indicated as mean±SEM (n=15). Statistical analysis was carried out using the Student's test A NOVA and when possible the Bonferroni test (*$p > 0.05$;  $p > 0.01$; * $p > 0.005$; n.s., not significant). Results are indicated in the representative example of 4 or more individual experiments.

[Results]

We carried out mRNA genome wide screening in the osteoclasts and the osteoblasts using GeneChip analysis to study whether or not the semaphorin, ephrin, slits and netrin which are axon guidance molecules contribute to the remodeling of the bone. This means that after analyzing 20 kinds of semaphorin, 16 types of ephrin, 6 types of slits and 6 kinds of netrin, an extremely high manifestation of semaphorin 4D was confirmed in the osteoclasts. Meanwhile, this manifestation was not confirmed in the osteoblasts. These results indicate that the semaphorin 4D had a selectively induced manifestation in the osteoclast formation process.

Figure 2:
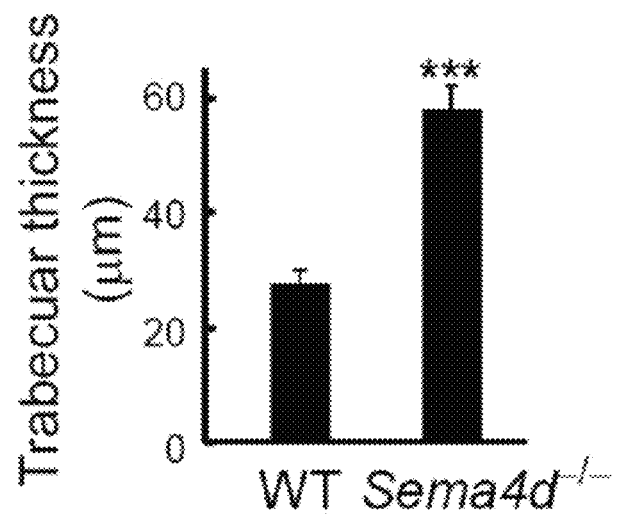
FIG. 2 A diagram indicating the trabecular width in WT mice measured using $\mu$CT and Sema4d-/- mice.
Figure 3:
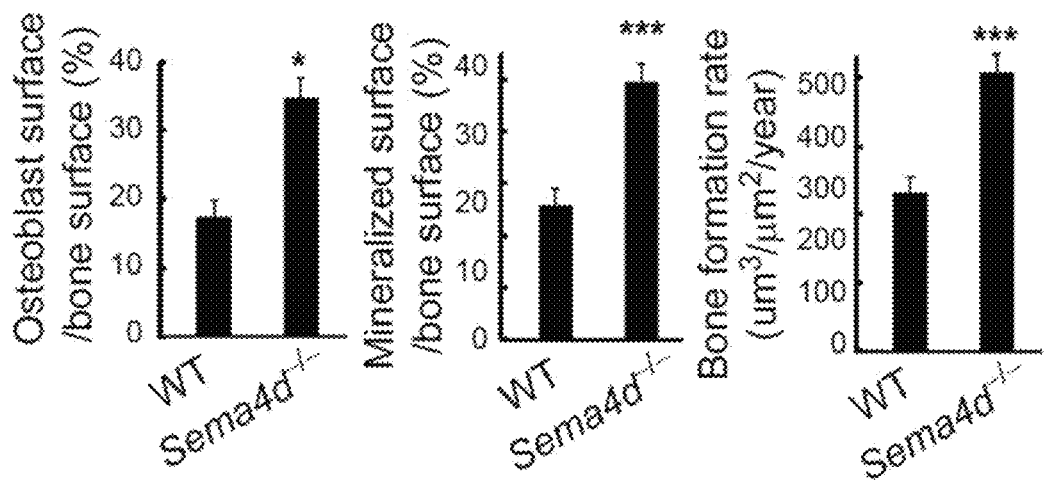
FIG. 3 A diagram indicating osteogenesis [surface area of osteoblast (left); surface area of calcified bone (center); and osteogenesis rate (right)] measured using osteomorphogenesis analysis in WT mice and Sema4d-/- mice with calcein double marker every 4 days.
Figure 4:
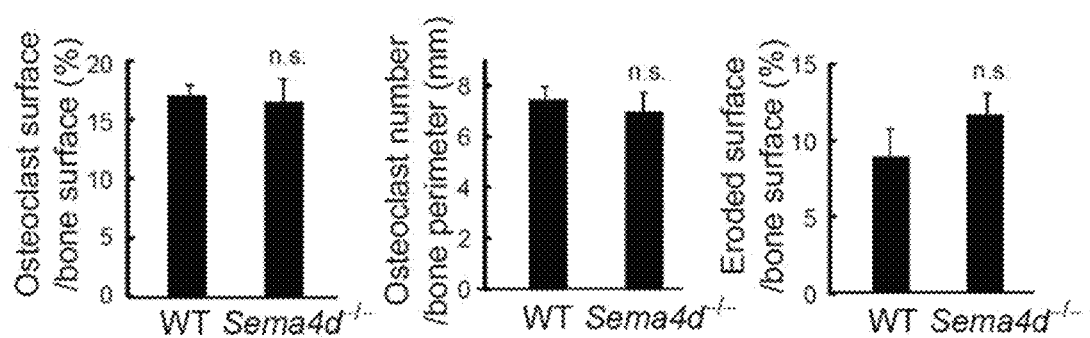
FIG. 4 A diagram indicating the osteoclast surface area and the cell count (at left and in the middle) as well as the parameters (at right) of the bone resorption measured using osteomorphogenesis analysis in WT nice and Sema4d-/- mice.

We carried out a functional analysis of the skeletal system using Sema4d-/- mice to study the semaphorin 4D function with selectively induced manifestation in the osteoclast formation process. The bone quantity (FIG. 1) and the trabecular width (FIG. 2) in the Sema4d-/- mice was shown to have increased significantly compared to the wild-type mice (WT mice) by using µCT and osteomorphogenesis analysis. The surface area of the osteogenesis in Sema4d-/- mice (FIG. 3, at left), the surface area of the calcified bone (FIG. 3, middle) and the osteogenesis rate (FIG. 3, at right) increased conspicuously as compared to the wild type mice. However, there were no changes in the parameters (surface areas of osteoclasts (FIG. 4, at left), the number of osteoclasts (FIG. 4, center) and the surface area of the corroded bone (FIG. 4, at right) indicating the bone resorption of the osteoclasts. We also observed that the in vitro osteoclast formation in Sema4d-/-cells was normal. Despite the fact that the semaphorin 4D manifested specifically in the osteoclasts, these results suggest that the phenotype of high bone density in the Sema4d-/- mice increased due to osteogenesis through the osteoblasts.

Figure 5:
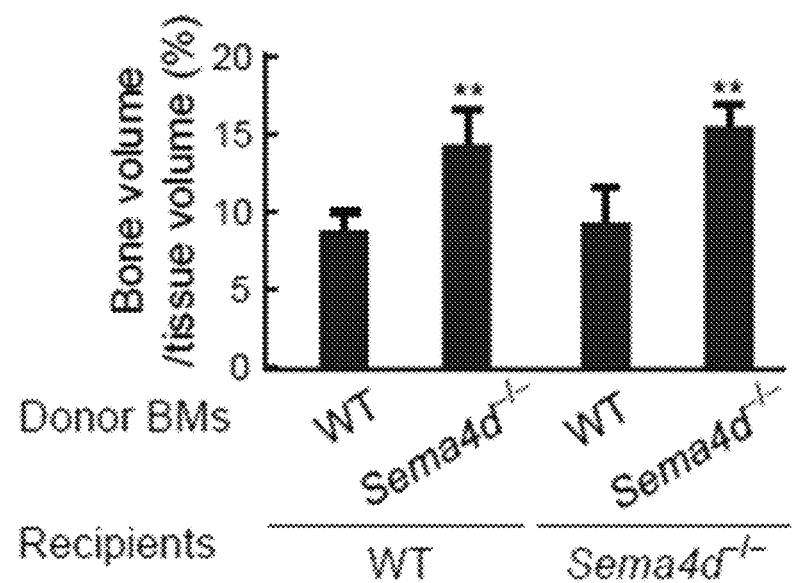
FIG. 5 A diagram indicating the bone quantity of mice in which adoptive immune cell grafting has been carried out using the bone marrow cells of WT mice and Sema4d-/- mice. The second graph from the left indicates the bone quantity of mice when grafted onto WT mice and the second graph from the right indicates the bone quantity of mice when grafted onto Sema4d-/- mice.
Figure 6:
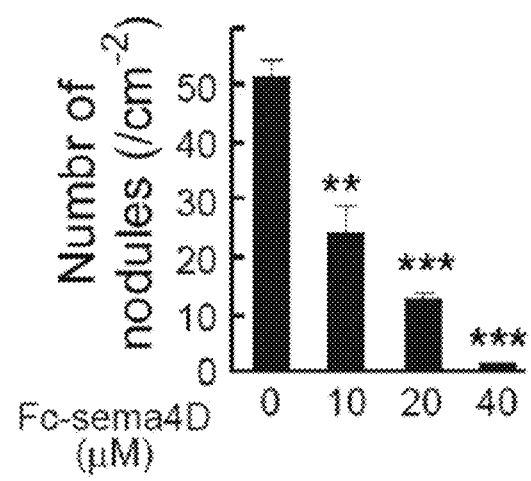
FIG. 6 A diagram indicating the number of bone nodes when Fc-sema4D (recombined Semaphorin 4D fused with the Fc area of the IgG1) are added to the calvarial cells cultured under the osteogenesis conditions.

We carried out adoptive immune cell grafting using bone marrow cells which included osteoclast precursor cells to find out whether or not the Sema4d-/- mice bone phenotype was based on abnormalities in the bone marrow cell system. As a result, the bone quantity increased when the Sema4d deficient bone marrow cells were grafted onto the wild mice as compared to when wild type bone marrow cells were grafted (see the two graphs on the left in FIG. 5), Meanwhile, when wild type bone marrow cells were grafted onto Sema4d-/- mice, the bone quantity decreased and returned to normal as compared to when the Sema4d deficient bone marrow cells were grafted (see the two graphs on the right in FIG. 5). Based on these results, it was indicated that the bone phenotype in the Sema4d-/- mice was such that abnormalities in the hematopoietic system cells comprising the osteoclasts were the cause. Furthermore, no clear-cut increase in the osteonodes of the Sem4d-/- calvarial cells was confirmed in the osteonodosity of the Sema4d-/- calvarial cells. These results suggest that the semaphorin 4D which manifests in the osteoclasts functions as a bone remodeling factor inhibiting osteogenesis through the osteoblasts.

We produced Fc-sema4D (I. Ishida et al., Int Immunol 15, 1027 (August, 2003) to study in detail the inhibition effect of the semaphorin 4D on the osteoblasts. Then, we added the Fc-sema4D to the calvarial cells which had been cultured under osteogenesis conditions. Adding the Fc-sema4D inhibited concentration dependency activation of ALP and manifestation of osteocalcin [Bglap] and collagen I type [Colla1]). These results indicate that the osteonodosity is inhibited as a result of the Sema4D inducing differentiation of the osteoblasts. We also cultured the calvarial cells in the presence of the culturing supernatant of the osteoclasts or in the presence of the osteoblasts to see whether or not the semaphorin 4D derived from the osteoclasts contributed to the regulation of the osteogenesis. In joint culturing with the culture supernatant of the wild-type osteoclasts or with the osteoclasts, there was no effect on the osteonodosity whereas in joint culturing with the culture supernatant of the Sema4d-/- osteoclasts or in joint culturing with the osteoclasts, osteonodosity was clearly accelerated. Based on these results, the osteoclasts are indicated as inhibiting osteogenesis through the semaphorin 4D produced as soluble at least partially. It must also be pointed out that one or more factors are contained in the supernatant of the osteoclasts. The osteogenesis acceleration effect brought about by these factors is thought to be brought out to the fullest when semaphorin 4D is not present.

Figure 7:
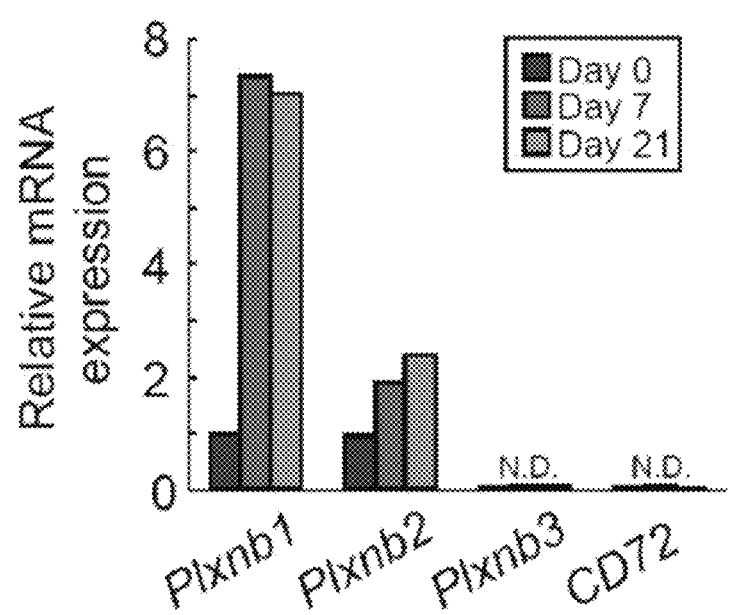
FIG. 7 A diagram indicating the manifestation of Plexin B type and mRNA of cluster of differentiation 72 (CD72) during osteoblast differentiation.
Figure 8:
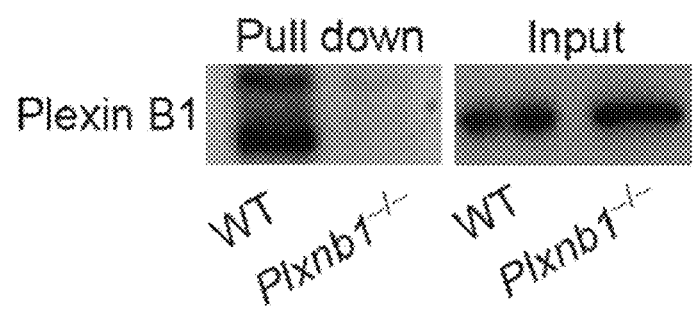
FIG. 8 A diagram indicating results of pull down analysis using Fc-sema4D. The panel on the right indicates results of sampling analysis prior to pull down and the panel on the left indicates results of sampling analysis alter pull down.
Figure 9:
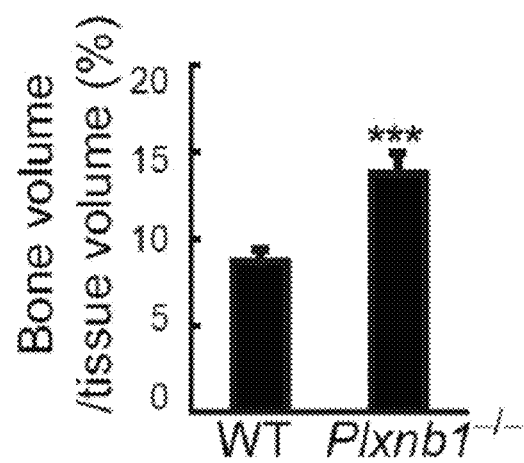
FIG. 9 A diagram indicating the bone quantity in WT mice measured using $\mu$CT analysis and in Plexin B1 knockout (Plxnb1-/-) mice.
Figure 10:
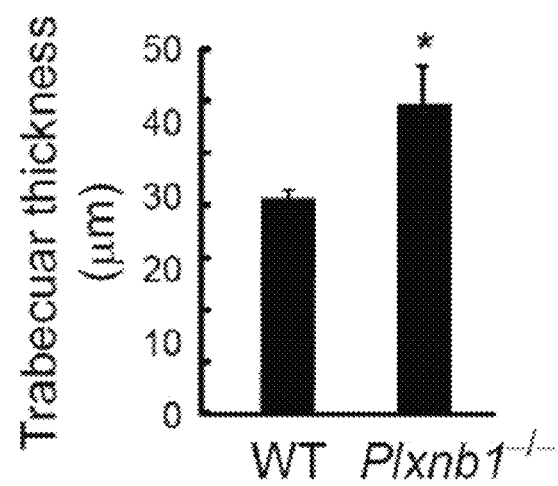
FIG. 10 A diagram indicating the width of the trabecula in WT mice measured using $\mu$CT mice and Plxnb1-/- mice.
Figure 11:
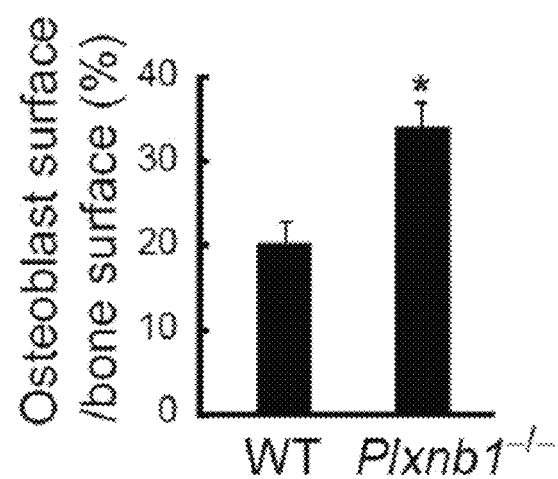
FIG. 11 A diagram indicating the surface area of osteoblasts h WT mice measured using osteomorphogenesis analysis.
Figure 12:
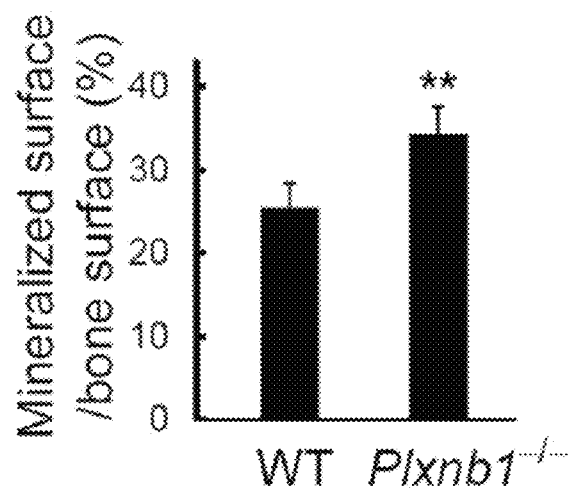
FIG. 12 A diagram indicating bone surface area which has become calcified in WT mice measured using osteomorphogenesis analysis and Plxnb1-/- mice.
Figure 13:
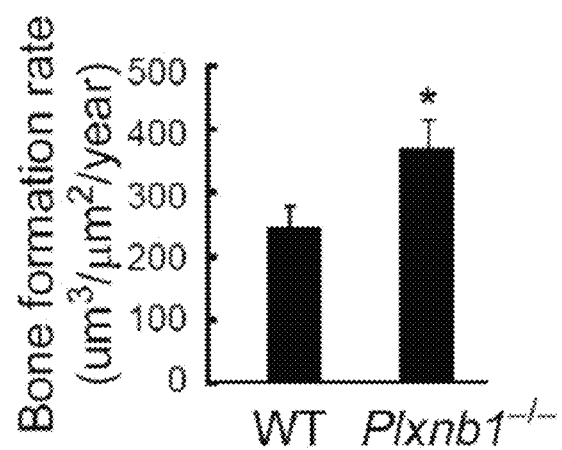
FIG. 13. A diagram indicating the osteogenesis rate in WT mice measured using osteomorphogenesis analysis and Plxnb1-/- mice.

We analyzed (a) the manifestation of the plexin B type which is well known as a semaphorin D receptor in non-lymphatic cells and lymph cells and (b) the RNA of CD72 (K. Suzuki, A. Kumanogoh, H. Kikutani, Nat Immunol 9, 17 (January, 2008) using quantitative real time RT-PCR in order to specify the semaphorin 4D receptor where the osteoblasts manifested. As a result, the amount, of plexin B1 manifested increased conspicuously during osteoblast differentiation (FIG. 7). Meanwhile, the amount, of plexin B2 manifested was rather low and there was virtually no manifestation plexin B 3 and CD 72 (FIG. 7). After carrying out pull down analysis using Fc-sema 4D, it was indicated that the semaphorin 4D interacted with plexin B1 (FIG. 8). It was also indicated that Fc-sema 4D induces phosphorylation of plexin B 1. It is well known that when semaphorin 4D binds with plexin B1, a conjugate is formed with tyrosine kinase ErbB2 and ErbB2 phosphorylizes itself and plexin B1 is dependent on semaphorin B4. In osteogenesis, after inhibiting ErbB2 kinase activation, the phosphorylation declines dependent on the semaphorin 4D stimulation of plexin B1. Based on these results, it is suggested that the plexin B1 acts as the main receptor for the semaphorin 4D in the osteoblasts. Then, we analyzed the bone phenotype of the Plxb1--/- mice. Like the Sema4d-/- mice, the bone quantity (FIG. 9) and the width of the trabecula (FIG. 10) of the Plxnb1-/- mice increase conspicuously as compared to the wild type mice due to an increase in the osteoblast osteogenesis. The surface area of the osteoblasts in the Plxnb1-/- mice (FIG. 11), the surface area of the calcified bone (FIG. 12) and the osteogenesis rate (FIG. 13) also increased respectively as compared to the wild-type mice. However, there was no change in the parameters (surface area of the osteoclasts, osteoclast cell count and corrosion of bone surface area) indicating the bone resorption in the osteoclasts. Based on these results, it is suggested that the phenotype of high bone density of the Plxnb1-/- mice, like the phenotype of the high bone density of the Sema4d-/- mice, is caused by an increase in osteogenesis brought about by the osteoblasts. No stimulation effect on the osteonodosity by the osteoblasts confirmed by the wild-type Sema4d-/- osteoclasts was confirmed with the Sem4d-/- osteoclasts. Therefore, this suggests that plexin B1 recognizes the osteogenesis mainly through semaphorin 4D.

Figure 14:
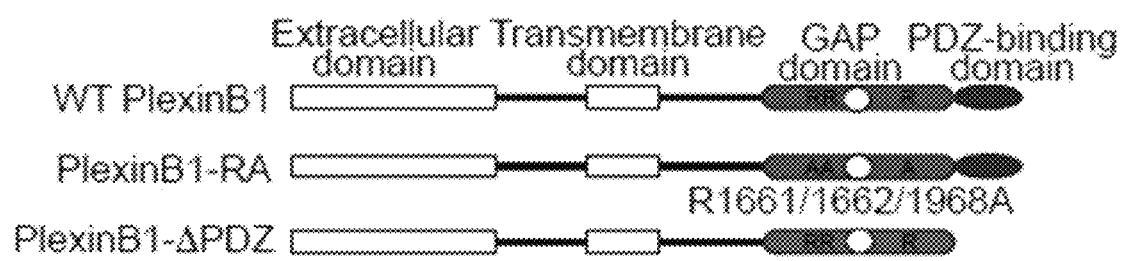
FIG. 14 A diagram indicating RA mutants (R1661/1662/1968A) of Plexin B1 and Plexin B1 having mutations in the GAP domain as well as the mutant cut for Plexin B1 in which the PDZ bond domain is missing (ΔPDZ).

How does the semaphorin 4D-plexin B1 transform to the inhibition signals in the osteoblasts? It is well known that the semaphorin-plexin system regulates osteomorphogenesis and cell wandering by regulating the rearrangement of the actin cell bone. It is also well known that when semaphorin 4D is combined with plexin B2, the RhoA activity is stimulated in the presence of tyrosine kinase ErbB2 whereas the semaphorin 4D has a counter action in the presence of other tyrosine kinase Met (J. M. Swiercz, T. Worzfeld, S. Offermanns, J Bio Chem 283, 1893 (Jan. 25, 2008). Therefore, we studied, the possibility of semaphorin 4D activating the RhoA. When we analyzed the amount of ErbB2 and Met manifested in the osteogenesis, it was suggested that EbrB2 manifested in considerably greater quantities than the Met. Although semaphorin 4D stimulation induced phosphorylation of the ErbB2, phosphorylation of Met was not induced. Furthermore, based on immunoblotting analysis and pull down analysis, semaphorin 4D increased the GTP combining activation type for RhoA and it is indicated that this activity is inhibited particularly by the Plxnb1-/0 cells. Meanwhile, the activity of Rac1 which is in another Rho family did not affect the semaphorin 4D stimulation. Coinciding with these results, when we introduced structured activation type RhoA using an adenovirus, the osteonodosity in the calvarial cells was inhibited whereas when dominant negative RhoA was introduced, the osteonodosity was accelerated. Meanwhile, the structured activation type Rac1 and the dominant negative Rac1 did not affect the osteogenesis. Based on these results, it is suggested that the KhoA selectively mediates the inhibition effect for the osteogenesis of semaphorin 4D-plexin B1. Plexin B1 has two RhoGTPase regulation domains, that is, a GTPase activated protein (GAP) domain and a PDZ-binding domain which binds to Rho-GEF (I. Oinuma, Y. Ishikawa, H. Katoh, M. Negishi, Science 305, 862 (Aug. 6, 2004), J. M. Swiercz, R. Kuner, J. Behrens, S. Offermanns, Neuron 35, 51 (Jul. 3, 2002), V. Perrot, J. Vazquez-Prado, J. S. Gutkind, J Bio Chem 277, 43115 (Nov. 8, 2002), M. H. Driessens, C. Olivo, K, Nagata, M. Inagaki, J. G. Collard. FEBS Lett 529, 168 (Oct. 9, 2002). Based on pull down analysis and immunoblotting analysis, PDZ-RhoGEF and LARG (leukemia associated RhoGEF) which are known as Rho-GEG were indicated as binding with plexin B1 even in the osteoblasts. Therefore, the abovementioned GAP domain and PDZ-binding domain produced two types of plexin B1 mutants (Plexin B1-Δ PDZ and Plexin B1•RA) to determine whether the osteoporosis was significantly inhibited (I. Oinuma, Y. Ishikawa, H. Katoh, M. Negishi, Science 305, 862 (Aug. 6, 2004) (FIG. 14). After the two types of plexin B1 mutants and wild type plexin B1 (WT-Plexin•B1) were used respectively to produce Plxnb1-/- calvarial cells with excess manifestation, we stimulated these using Fc-sema 4D and evaluated the osteoblast differentiation inhibition effect. The inhibition effect of the Fc-Sema4d indicated in the manifestation of mRNA of the osteoblast markers (Alpl, Bglap and Colla1) was recovered in the WT-Plexin B1 and PlexinB1-RA excess manifestation, however, it was not recovered in the PlexinB1-Δ PDZ excess manifestation. These results suggest that RhoA mediates the inhibition of osteogenesis specifically by the semaphorin 4D.

Figure 15:
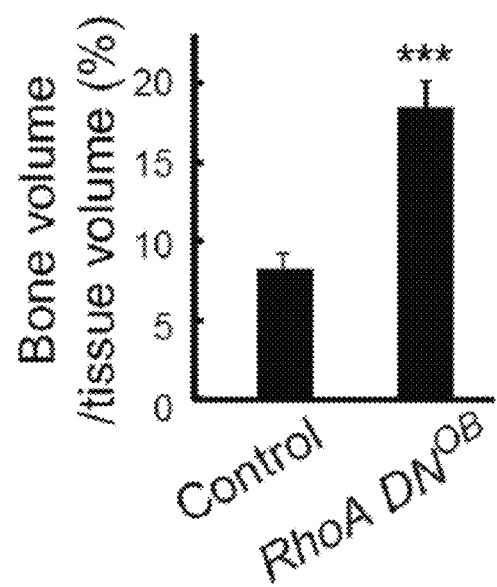
FIG. 15 A diagram indicating the bone quantity in WT mice (control mice) measured using μCT analysis and dominant negative RhoA (RhoA DNOB) mice.
Figure 16:
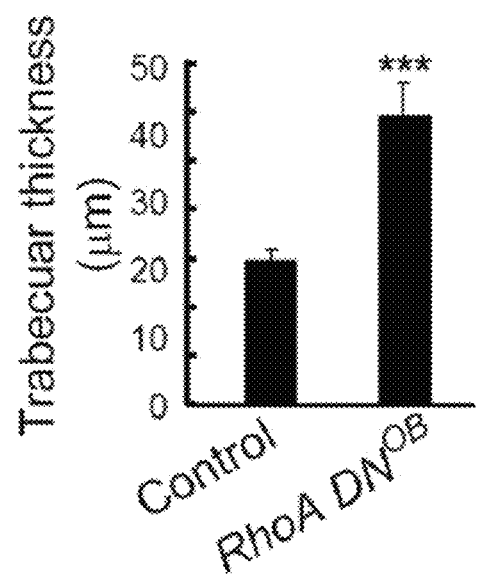
FIG. 16 A diagram indicating the trabecula in WT mice measured using μCT analysis and RhoA DNOB.
Figure 17:
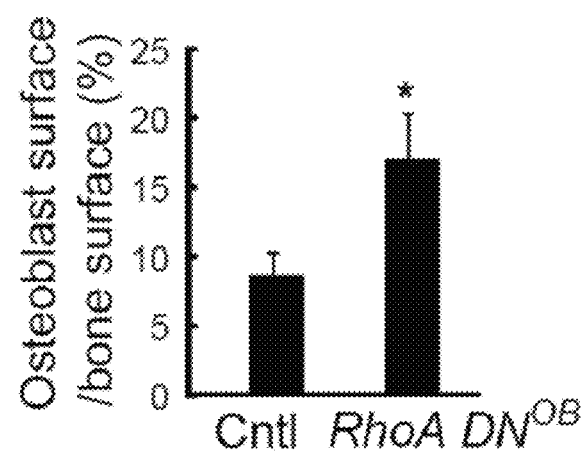
FIG. 17 A diagram indicating the formation [osteoblast surface area] in WT mice and RhoA DNOB mice measured using osteomorphogenesis analysis.
Figure 18:
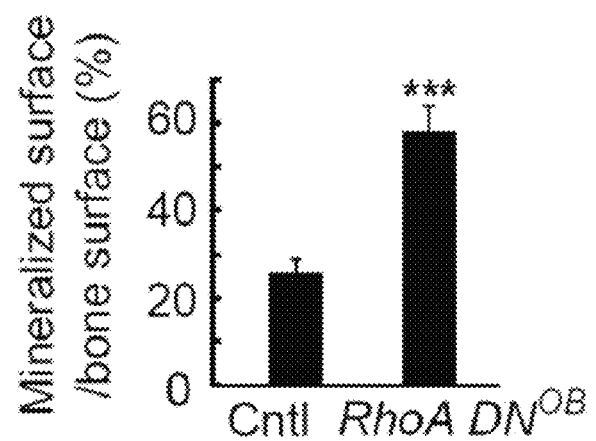
FIG. 18 A diagram indicating the formation, [surface area of calcified bone] of WT mice and RhoADNOB mice.
Figure 19:
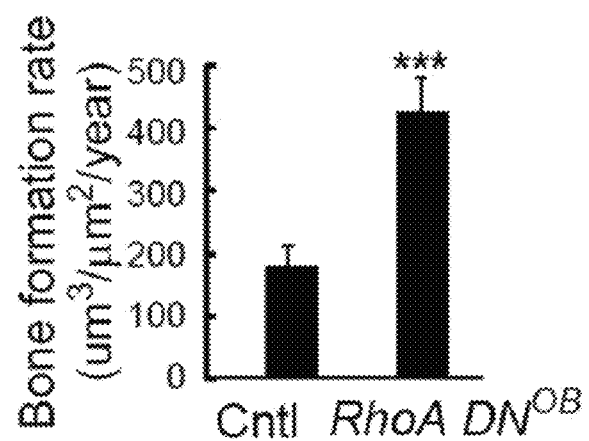
FIG. 19 A diagram indicating the formation [osteogenesis rate] in WT mice and RhoA DNOB mice measured using osteomorphogenesis analysis.

We crossed CAT-RHoA DN transgenic mice (K. Kobayashi et ah, J. Neurosci 24, 3480 (Apr. 7, 2004) and collagen α 1 (I)-Cre transgenic mice (R. Dacquin, M. Starbuck, T. Schinke, G. Karsenty, Dev. Dyn 224, 245 (June, 2002)) and produced mice in which dominant negative RhoA was manifested specifically (RhoA DNOB) in the osteoblasts to study the role of RhoA in the osteoblasts in vivo. The bone quantity (FIG. 15) and the width of the trabecula (FIG. 16) of the RhoA DNOB mice increased as compared to the wild type mice when osteogenesis was accelerated by the osteoblasts. In addition, the surface area of the osteoblasts (FIG. 17) of RhoA DNOB mice, the surface area of the bone (FIG. 18) which had calcified and the osteogenesis rate (FIG. 19) increased conspicuously compared to the wild-type mice, however, there were no changes in the parameters which indicated the bone resorption of the osteoclasts (surface area of osteoclasts, number of osteoclasts and surface area of corroded bone). The bone phenotype was the same as the bone phenotype for the Sema4d-/- and Plxb1-/- mice. As the manifestation of the RhoA DNOB increased during osteoblast differentiation, the manifestation of the osteonodosity and osteoblast marker genes (Alpa, Bglap and Colla1) increased markedly in the calvarial cells originating in the RhoA DNOB mice. The osteonodosity which increased in the RhoA DNOB cells was not inhibited by the Fc-sema4d so that it is suggested that the RhoA mediates the inhibition signals downstream of the semaphorin 4D-plexin B1.

Figure 20:
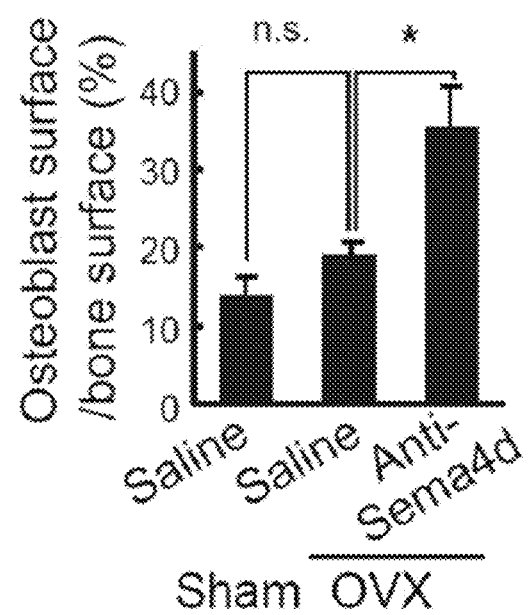
FIG. 20 A diagram indicating the surface area of osteoblasts of mice with extracted ovaries (OVX) and OVX mice treated with anti-Sema4D bodies measured using osteomorphogenesis analysis.
Figure 21:
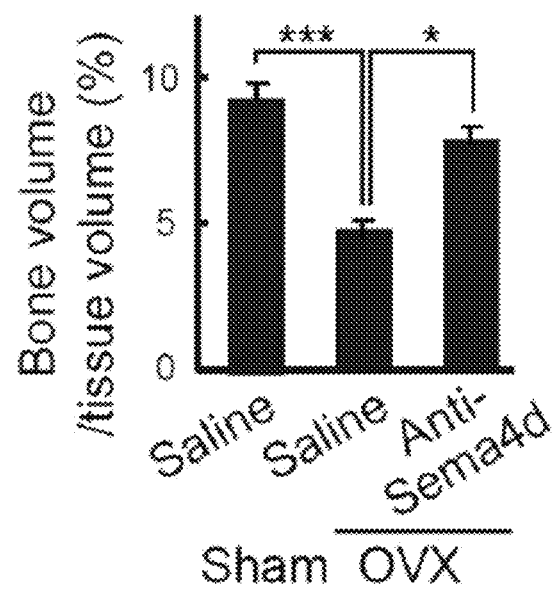
FIG. 21 A diagram indicating the bone quantity of OVX mice and OVX mice treated with anti-semaphorin 4D antibodies (anti-Sema4D antibodies) measured using μCT analysis.
Figure 22:
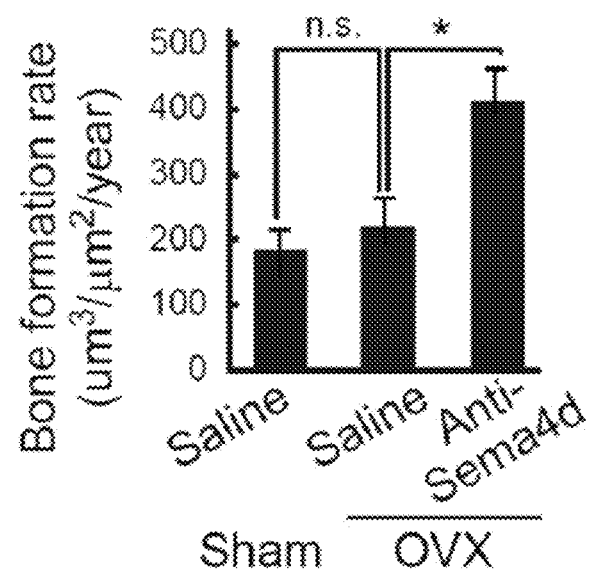
FIG. 22 A diagram indicating the osteogenesis [osteogenesis rate] in OVX mice and in OVX mice treated with anti-Sema4D antibodies measured using osteomorphogenesis analysis.
Figure 23:
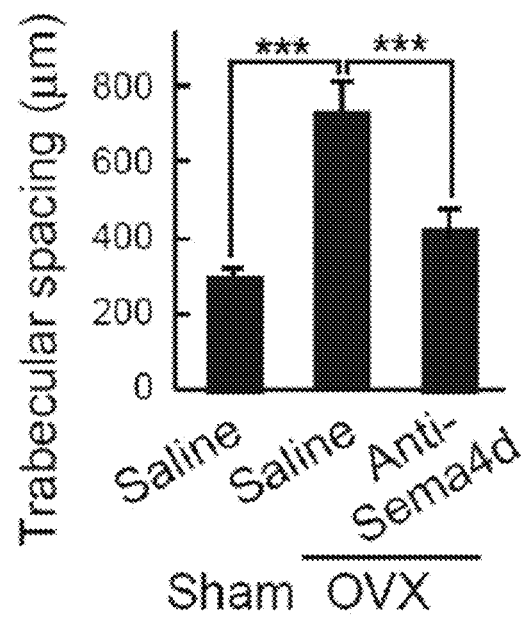
FIG. 23 A diagram indicating the trabecular intervals in OVX mice and in OVX mice treated with anti-Sema4D antibodies measured using μCT analysis.
Figure 24:
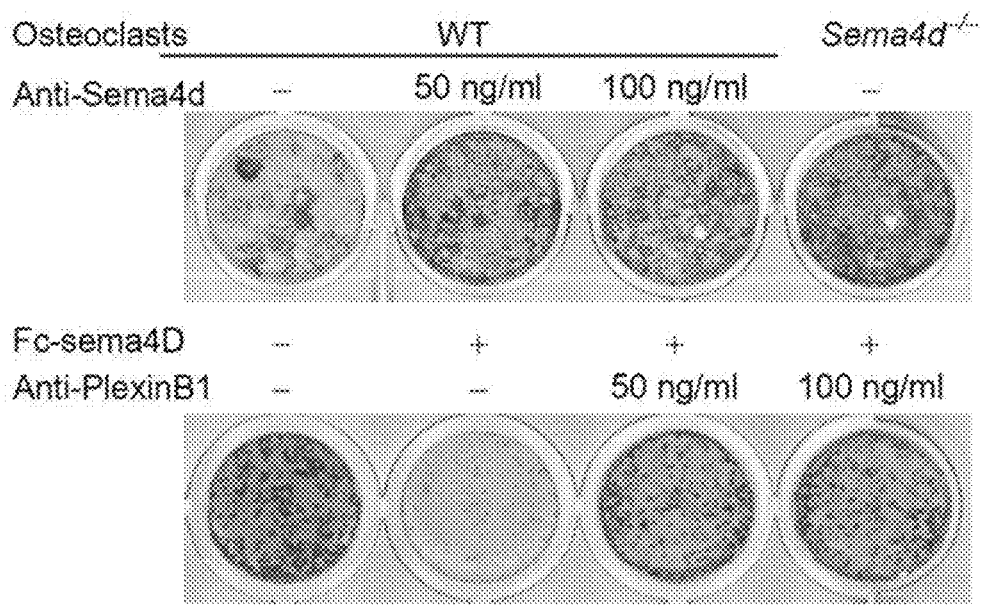
FIG. 24 The upper panel in FIG. 24 is a diagram indicating results of studying the calcification formation of mice osteoblasts cultured using osteoclasts of WT mice of Sema4D-/- mice and when cultured in the presence of anti-Sema4D antibodies. The lower panel in FIG. 24 is a diagram indicating the results of studying the calcification of mouse osteoblasts when cultured in the presence of Fc-sema4d and/or anti-plexin Ba antibodies.
Figure 25:
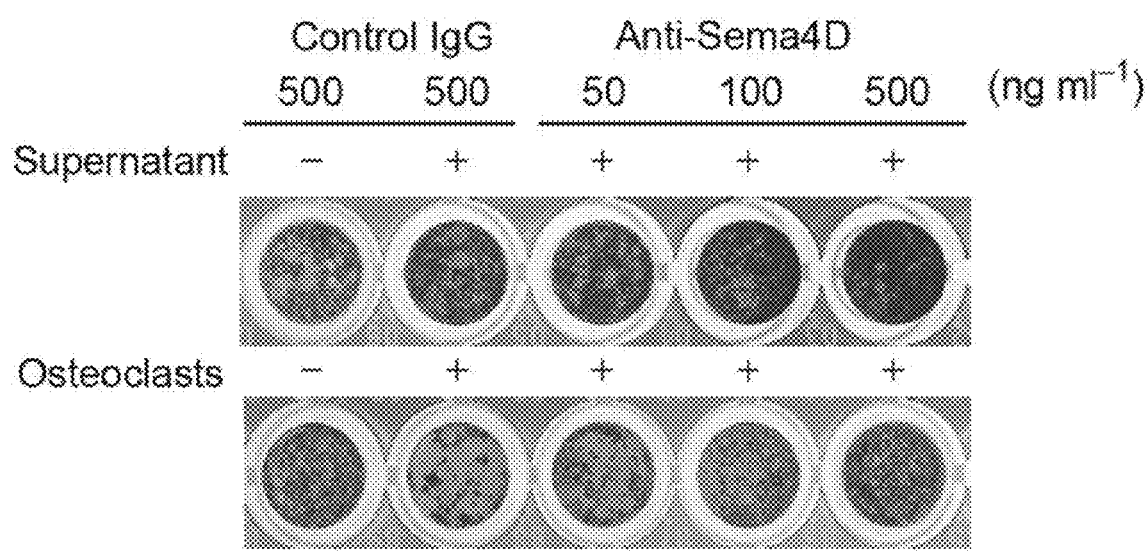
Figure 26:
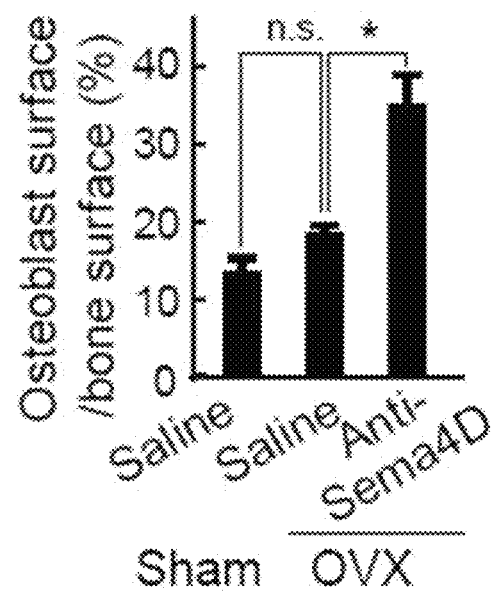
FIG. 26 A diagram indicating the surface area of osteoblasts of mice with extracted ovaries (OVX) and OVX mice treated with anti-semaphorin 4D antibodies (anti-Sema4D antibodies) 6 weeks after OVX treatment, measured using osteomorphogenesis analysis.
Figure 27:
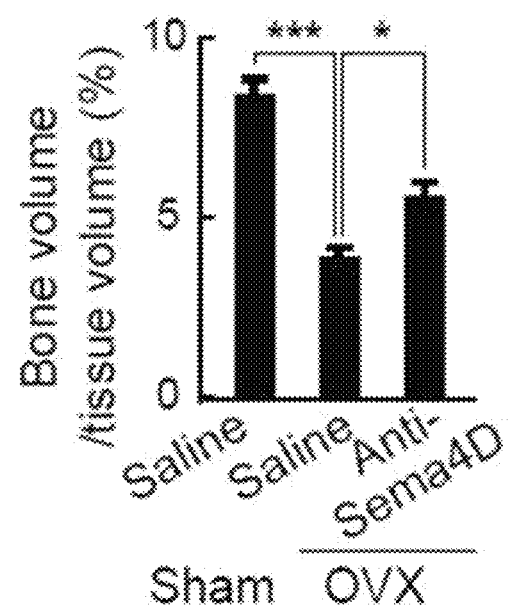
FIG. 27 A diagram indicating the bone quantity of OVX mice and OVX mice treated with anti-Sema4D antibodies 6 weeks after OVX treatment measured using μCT analysis.
Figure 28:
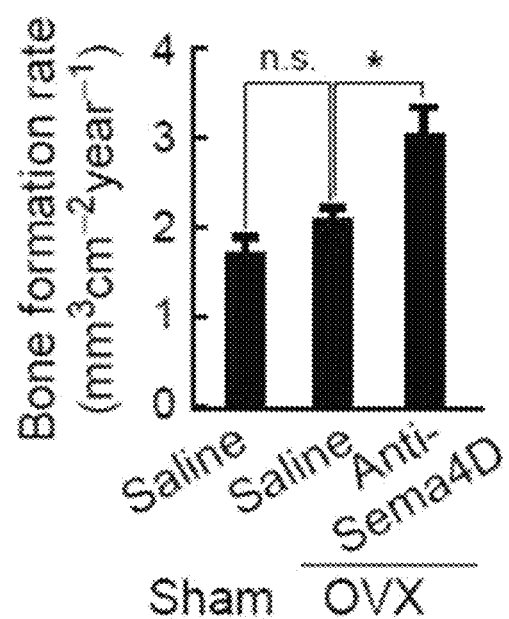
FIG. 28 A diagram indicating the osteogenesis [osteogenesis rate] in OVX mice and in OVX mice treated with anti-Sema4D antibodies 6 weeks after OVX treatment measured using osteomorphogenesis analysis.
Figure 29:
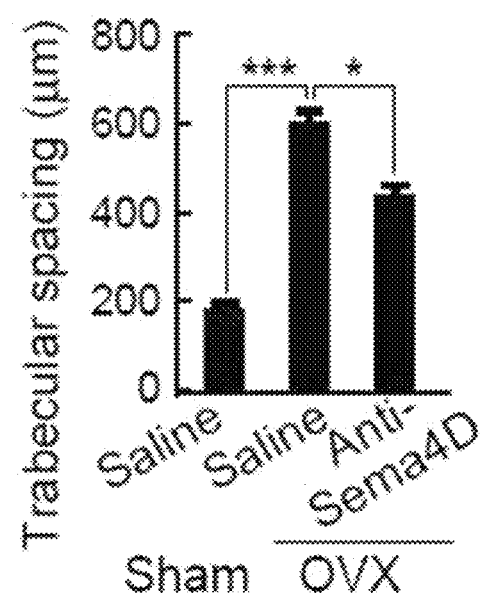
FIG. 29. A diagram indicating the trabecular intervals in OVX mice and in OVX mice treated with anti-Sema4D antibodies 6 weeks after OVX treatment measured using μCT analysis.

In order to study whether or not the Sema4D function inhibition was effective for osteoporosis, we carried out validation using model mice with osteoporosis after menopause treated for OVX (ovaries excised). This means that we administered intravenously the anti-Sema4D antibodies in mice on a weekly basis following OVX treatment and studied whether there was a preventive effect for a decrease in bone quantity. After analyzing the bone tissue, the bone quantity decreased when anti-Sema4d antibodies were not administered whereas when anti-Sema4d antibodies were administered, acceleration in osteogenesis (increase in surface area of osteoblast. [FIG. 20], bone quantity [FIG. 21] and osteogenesis rate [FIG. 22] and decrease in trabecular intervals [FIG. 23]) was confirmed. Meanwhile, there were no changes in the parameters indicating bone resorption of the osteoclasts (number of osteoclasts and surface area of corroded bone). Based on these results, when the function of semaphorin 4D is inhibited by anti-Sema 4D antibody treatment, a preventive effect, on the decrease in bone quantity in osteoporosis is indicated. We also studied whether or not the functional inhibition of semaphorin 4D was effective even for treatment of bone quantity which had already decreased. This means that after OVX treatment, we administered the anti-Sema4d antibodies from the caudal vein for three weeks three times a week 6 weeks after the bone quantity had decreased. The results of analyzing the parameters indicating osteogenesis (surface area of osteoblasts, increase in bone quantity, increase in osteogenesis rate and decrease in trabecular intervals) confirmed acceleration in osteogenesis (increase in surface area of osteoblast [FIG. 26], bone quantity [FIG. 27] and osteogenesis rate [FIG. 28] and decrease in trabecular intervals [FIG. 29]). Therefore, it became clear that once the bone quantity had decreased it returned to the same level as when Sema4D antibodies were administered on a weekly basis after the abovementioned OVX treatment. This means there was a return to the same level as when decrease in bone quantity was prevented. Meanwhile, there were no changes in the parameters indicating bone resorption of the osteoclasts (surface area of corroded bone). We also studied the effect of the functional inhibition of semaphorin 4D and plexin B1 on osteonodosity. When mouse osteoblasts and the osteoclasts of WT mice were used, osteonodosity was accelerated as a function of the concentration of anti-Sema 4D antibodies (plates 1 to 3 from the left in the upper panel of FIG. 24). Meanwhile, the osteonodosity which was inhibited by Fc-sema4d was accelerated as a function of the concentration of anti-plexin B1 antibodies (lower panel in FIG. 24). Based on these results, when the semaphorin 4D-plexin B1 interaction is inhibited by anti-Sema 4d antibody treatment or anti-plexin B1 antibody treatment, not only is the decrease in bone quantity in osteoporosis inhibited but an effect, which promotes an increase in bone quantity is indicated as well. We also studied the effect of the functional inhibition of semaphorin 4D in human osteoblasts on osteonodosity. This means that when we carried out validation using osteoclasts which had differentiated from the human peripheral blood monocyte derived CD14 positive cells (FIG. 25, lower row) and the culturing supernatant thereof (FIG. 25, upper row) and when we added it to the osteoclasts and the culturing supernatant thereof and added anti-Sema4d antibodies to the osteoblasts, the osteonodosity was accelerated as a function of the concentration of the anti-Sema 4d antibodies (FIG. 25). These results indicate that the results in the abovementioned post-menopausal osteoporosis model mice were supported in human cells and that inhibition of the semaphorin 4D-plexin B1 interaction is a new strategy in promoting osteogenesis.

We made a detailed analysis of the action of the semaphorin RD osteoblast differentiation inhibition. This means that when we compared the number of hematopoietic cells in the bone marrow (Sca-1+CD105+CD106+CD44+CD45, 2-CD11b) in the Sema4d-/- mice with the wild-type mice by carrying out flow cytometry analysis, there were no differences. We also carried out cell proliferation analysis and although there was somewhat of an increase due to the Sema4d prior to the differentiation of the osteoblasts (Day 0), there were no changes due to the semaphorin 4D stimulation in the osteoblast differentiation process (Day 14). Furthermore, based on CFU analysis, the osteogenesis indicated in the ALP manifestation and the alizarin was inhibited due to the semaphorin 4D stimulation. These results suggest, that the semaphorin 4D acts in osteoblast differentiation stages.

Insulin receptor substrate (IRS) signals caused by insulin-like growth factors (IGF)-1 are known to accelerate the differentiation of the osteoblasts. Therefore, we studied Akt and ERK phosphorylation relating to the IRS signals with semaphorin 4D stimulation and the phosphorylation level declined. The Tyr phosphorylation which is the IRS activation indicator also declined. These results suggest that semaphorin 4D stimulation decreases the IRS signals, it is also clear that the activated type RhoA lowers the Akt and ERK phosphorylation and conversely Y-27632 and RKI which are RhoA inhibitors promote this phosphorylation. It is also clear that the RhoA inhibitor induces the promotion of activation type phosphorylation in the IRS signals. These results suggest that semaphorin 4D induces a decline in IRS signals by activating the RhoA and inhibits osteoblast differentiation.

[Summary]

Based on the abovementioned experiments, we identified osteoclast-derived semaphorin 4D as an extremely important mediator for transmission between osteoclasts-osteoblasts in bone reconstruction. Bone reconstruction is carried out in cycles made up of three stages (beginning of bone resorption due to osteoclasts, transition to new osteogenesis due to osteoblasts and completion of new bone synthesis (K. Matsuo, N. Irie, Arch Biochem Biophys 473, 201 (May 2008). Semar4d which manifests in osteoclasts functions up to the time osteoclast resorption is completed as an osteogenesis inhibition factor in the initial stage in which, differentiation of the osteoblasts is inhibited. Furthermore, activation of RhoA is also indicated as inhibiting osteoblast osteogenesis in vivo. EphrinB2/EphB4 indicated as contributing to the transition stage also make use of RhoA to regulate the osteogenesis (C. Zhao et al., Cell Metab 4, 111 (August, 2006) which suggests that the Rho family-lower molecular GTPase acts as a coordinator for bone reconstruction single transmission. The PDZ-containing RhoA specific GEFArfgef 12 (LARG) (J. M. Swiercz, R. Kuner, J. Behrens, S. Offermanns, Neuron 35, 51 (Jul. 3, 2002); V. Perrot, J. Vazquez-Prado, J. S. Gutkind, J Bio Chem 277, 43115 (Nov. 8, 2002)) has been indicated to have high, manifestation in osteoblasts in GeneChip analysis. These results back up the importance of the semaphorin 4D-plexin B1-RhoA path. Furthermore, based on analysis using immunofluorescent staining, a down regulation for cadherin 11 has been observed after Fc-ema Rd stimulation and the contribution of the regulated gap binding function is suggested. Intermittent, parathyroid hormones (PTH) treatment is the only effective method which has been proved to increase osteogenesis. Anti-Sost antibodies which are currently in development have garnered attention as a novel osteogenesis agent while antibodies targeting factors related to the semaphorin 4D-plexin B1-RhoA path and inhibitors and the like can be expected to be new therapeutic agents for patients with osteopenia.

[Industrial Applicability]

The present invention can be used to effect in accelerating osteogenesis and in the prevention and treatment of bone diseases.

[Sequence Table]

Patent Application P11-0052011-108642_0.app

The invention claimed is:

1. A method for treating a bone disease characterized by insufficient osteogenesis or excessive bone resorption, comprising administering to a subject in need of treatment an effective amount of an anti-semaphorin 4D antibody or antigen-binding fragment thereof or an anti-plexin B1 antibody or antigen-binding fragment thereof, wherein the antibody or fragment thereof can inhibit binding of semaphorin 4D and plexin B1.

2. The method of claim 1, wherein the antibody or fragment thereof is monoclonal.

3. The method of claim 1, wherein the fragment of the antibody is an F(ab')$_2$ fragment, an Fab' fragment, an Fab fragment, an FIT fragment, a disulphide-linked FV fragment, a single-chain FV (scFV) fragment, or a polymer of one or more of said fragments.

4. The method of claim 1, wherein the antibody or fragment thereof is a human antibody.

5. The method of claim 1, wherein the bone disease is bone fracture, bone deficiency, osteoporosis, osteomalacia, osteopenia, lumbar pain, Paget's disease of bone, tonic myelitis, articular rheumatism, deformative arthrosis, or a combination thereof.

6. The method of claim 1, wherein the antibody or fragment thereof is administered orally, by vascular administration, by intravenous administration, by muscular administration, by hypodermic administration, by transdermal administration, by nasal administration, by transpulmonary administration, or any combination thereof.

7. The method of claim 1, wherein the subject is a mammal.

8. The method of claim 7, wherein the subject is a human.

9. A method to identify a candidate active ingredient for an osteogenesis acceleration agent, comprising:
   (a) contacting semaphorin 4D and plexin B1 in the presence of the candidate active ingredient;
   (b) measuring the degree of binding between semaphorin 4D and plexin B1;
   (c) comparing the degree of binding with the candidate active ingredient to the degree of binding between semaphorin 4D and plexin B1 when not in the presence of the candidate active ingredient;
   (d) identifying the candidate active ingredient as an osteogenesis acceleration agent when the degree of binding between semaphorin 4D and plexin B1 in the presence of candidate active ingredient is lower than the degree of binding between semaphorin 4D and plexin B1 when not in the presence of the candidate active ingredient.

10. A method for accelerating osteogenesis, comprising contacting osteoblasts with an anti-semaphorin 4D antibody or antigen-binding fragment thereof or an anti-plexin B1 antibody or antigen-binding fragment thereof, wherein the antibody or fragment thereof can inhibit binding of semaphorin 4D and plexin B1.

11. The method of claim 10, wherein the antibody or fragment thereof is monoclonal.

12. The method of claim 10, wherein the fragment of the antibody is an F(ab')$_2$ fragment, an Fab' fragment, an Fab fragment, an Fv fragment, a disulphide-linked FV fragment, a single-chain FV (scFV) fragment, or a polymer of one or more of said fragments.

13. The method of claim 10, wherein the antibody or fragment thereof is a human antibody.

14. The method of claim 10, wherein the antibody or fragment thereof can inhibit the suppression of differentiation of the osteoblasts.

15. The method of claim 1, wherein the treatment can prevent a decrease in bone quantity.

* * * * *

SEQUENCE LISTING

<160> NUMBER OF SEQ ID NOS: 20

<210> SEQ ID NO 1
<211> LENGTH: 2217
<212> TYPE: DNA
<213> ORGANISM: Homo sapiens

<400> SEQUENCE: 1

```
atgaggatgt gcaccccat aggggctg ctcatggccc ttgcagtgat gtttgggaca      60
gcgatggcat ttgcacccat accccggatc acctgggagc acagagaggt gcacctggtg     120
cagtttcatg agccagacat ctacaactac tcagccttgc tgctgagcga ggacaaggac     180
accttgtaca taggtgcccg ggaggcggtc ttcgctgtga acgcactcaa catctccgag     240
aagcagcatg aggtgtattg gaaggtctca gaagacaaaa aagcaaaatg tgcagaaaag     300
gggaaatcaa aacagacaga gtgcctcaac tacatccggg tgctgcagcc actcagcgcc     360
acttcccttt acgtgtgtgg gaccaacgca ttccagccgg cctgtgacca cctgaactta     420
acatccttta agtttctggg gaaaaatgaa gatggcaaag gaagatgtcc ctttgaccca     480
gcacacagct acacatccgt catggttgat ggagaacttt attcggggac gtcgtataat     540
tttttgggaa gtgaaccat catctcccga aattcttccc acagtcctct gaggacagaa      600
tatgcaatcc cttggctgaa cgagcctagt ttcgtgtttg ctgacgtgat ccgaaaaagc     660
ccagacagcc ccgacggcga ggatgacagg gtctacttct tcttcacgga ggtgtctgtg     720
gagtatgagt ttgtgttcag ggtgctgatc ccacggatag caagagtgtg caaggggggac     780 cagggcggcc tgaggaccct gcagaagaaa tggacctcct tcctgaaagc ccgactcatc     840
```

```
tgctcccggc cagacagcgg cttggtcttc aatgtgctgc gggatgtctt cgtgctcagg    900
tccccgggcc tgaaggtgcc tgtgttctat gcactcttca ccccacagct gaacaacgtg    960
gggctgtcgg cagtgtgcgc ctacaacctg tccacagccg aggaggtctt ctcccacggg   1020
aagtacatgc agagcaccac agtggagcag tcccacacca gtgggtgcg ctataatggc   1080
ccggtaccca agccgcggcc tggagcgtgc atcgacagcg aggcacgggc cgccaactac   1140
accagctcct tgaatttgcc agacaagacg ctgcagttcg ttaaagacca ccctttgatg   1200
gatgactcgg taaccccaat agacaacagg cccaggttaa tcaagaaaga tgtgaactac   1260
acccagatcg tggtggaccg gacccaggcc tggatgggga ctgtctatga tgtcatgttt   1320
gtcagcacag accggggagc tctgcacaaa gccatcagcc tcgagcacgc tgttcacatc   1380
atcgaggaga cccagctctt ccaggacttt gagccagtcc agaccctgct gctgtcttca   1440
aagaagggca acaggtttgt ctatgctggc tctaactcgg gcgtggtcca ggccccgctg   1500
gccttctgtg ggaagcacgg cacctgcgag actgtgtgc tggcgcggga ccctactgc   1560
gcctggagcc cgcccacagc gacctgcgtg gctctgcacc agaccgagag ccccagcagg   1620
ggtttgattc aggagatgag cggcgatgct tctgtgtgcc cggcctcgtc tcctaagccc   1680
ctccctcctc ctggctcctc ttccctgtcc tgtctgggcc atgtggggga caggaggctt   1740
tcctctccct ggaccccctg gccagcctcg ggtgcggggc ccgacagcag ctcgagggtc   1800
tccttgctgc cgcccttcct gagtgaccag gcacagcacg tgcacgccct ggggaacttc   1860
tacctcttct gccaggccac aggtcctgca gacattcgct ttgtctggga agaatggg   1920
cgagctctgg agacctgtgt ccctgtgcag acccatgcac tgcccgatgg cagggcccat   1980
gcactcagct ggctgcagga cgccatcagg gaaagcgctg agtatcgctg ctctgtcctc   2040
tcctcagcag gaacaagac ttcgaaggtg caggttgctg tgatgagacc tgaagtgacc   2100
caccaggaga ggtggaccag agagctctct gcctggaggg ctgtggctgg ggagcacgac   2160
cggatgatgc agagctggag gaaggcgtgg gaaagctgta gcaaggacac cctgtag     2217
```

<210> SEQ ID NO 2
<211> LENGTH: 738
<212> TYPE: PRT
<213> ORGANISM: Homo sapiens

<400> SEQUENCE: 2

```
Met Arg Met Cys Thr Pro Ile Arg Gly Leu Leu Ala Leu Ala Val
 1               5                  10                  15

Met Phe Gly Thr Ala Met Ala Phe Ala Pro Ile Pro Arg Ile Thr Trp
                20                  25                  30

Glu His Arg Glu Val His Leu Val Gln Phe His Glu Pro Asp Ile Tyr
            35                  40                  45

Asn Tyr Ser Ala Leu Leu Leu Ser Glu Asp Lys Asp Thr Leu Tyr Ile
        50                  55                  60

Gly Ala Arg Glu Ala Val Phe Ala Val Asn Ala Leu Asn Ile Ser Glu
65                  70                  75                  80

Lys Gln His Glu Val Tyr Trp Lys Val Ser Glu Asp Lys Lys Ala Lys
                85                  90                  95

Cys Ala Glu Lys Gly Lys Ser Lys Gln Thr Glu Cys Leu Asn Tyr Ile
                100                 105                 110

Arg Val Leu Gln Pro Leu Ser Ala Thr Ser Leu Tyr Val Cys Gly Thr
            115                 120                 125

Asn Ala Phe Gln Pro Ala Cys Asp His Leu Asn Leu Thr Ser Phe Lys
```

```
                130             135              140
Phe Leu Gly Lys Asn Glu Asp Gly Lys Gly Arg Cys Phe Asp Pro
145                 150                 155                 160

Ala His Ser Tyr Thr Ser Val Met Val Asp Gly Glu Leu Tyr Ser Gly
                    165                 170                 175

Thr Ser Tyr Asn Phe Leu Gly Ser Glu Pro Ile Ile Ser Arg Asn Ser
                180                 185                 190

Ser His Ser Pro Leu Arg Thr Glu Tyr Ala Ile Pro Trp Leu Asn Glu
                195                 200                 205

Pro Ser Phe Val Phe Ala Asp Val Ile Arg Lys Ser Pro Asp Ser Pro
210                 215                 220

Asp Gly Glu Asp Asp Arg Val Tyr Phe Phe Thr Glu Val Ser Val
225                 230                 235                 240

Glu Tyr Glu Phe Val Phe Arg Val Leu Ile Pro Arg Ile Ala Arg Val
                245                 250                 255

Cys Lys Gly Asp Gln Gly Gly Leu Arg Thr Leu Gln Lys Lys Trp Thr
                260                 265                 270

Ser Phe Leu Lys Ala Arg Leu Ile Cys Ser Arg Pro Asp Ser Gly Leu
                275                 280                 285

Val Phe Asn Val Leu Arg Asp Val Phe Val Leu Arg Ser Pro Gly Leu
290                 295                 300

Lys Val Pro Val Phe Tyr Ala Leu Phe Thr Pro Gln Leu Asn Asn Val
305                 310                 315                 320

Gly Leu Ser Ala Val Cys Ala Tyr Asn Leu Ser Thr Ala Glu Glu Val
                325                 330                 335

Phe Ser His Gly Lys Tyr Met Gln Ser Thr Val Glu Gln Ser His
                340                 345                 350

Thr Lys Trp Val Arg Tyr Asn Gly Pro Val Pro Lys Pro Arg Pro Gly
                355                 360                 365

Ala Cys Ile Asp Ser Glu Ala Arg Ala Ala Asn Tyr Thr Ser Ser Leu
                370                 375                 380

Asn Leu Pro Asp Lys Thr Leu Gln Phe Val Lys Asp His Pro Leu Met
385                 390                 395                 400

Asp Asp Ser Val Thr Pro Ile Asp Asn Arg Pro Arg Leu Ile Lys Lys
                405                 410                 415

Asp Val Asn Tyr Thr Gln Ile Val Val Asp Arg Thr Gln Ala Leu Asp
                420                 425                 430

Gly Thr Val Tyr Asp Val Met Phe Val Ser Thr Asp Arg Gly Ala Leu
                435                 440                 445

His Lys Ala Ile Ser Leu Glu His Ala Val His Ile Ile Glu Glu Thr
450                 455                 460

Gln Leu Phe Gln Asp Phe Glu Pro Val Gln Thr Leu Leu Leu Ser Ser
465                 470                 475                 480

Lys Lys Gly Asn Arg Phe Val Tyr Ala Gly Ser Asn Ser Gly Val Val
                485                 490                 495

Gln Ala Pro Leu Ala Phe Cys Gly Lys His Gly Thr Cys Glu Asp Cys
                500                 505                 510

Val Leu Ala Arg Asp Pro Tyr Cys Ala Trp Ser Pro Thr Ala Thr
                515                 520                 525

Cys Val Ala Leu His Gln Thr Glu Ser Pro Ser Arg Gly Leu Ile Gln
                530                 535                 540

Glu Met Ser Gly Asp Ala Ser Val Cys Pro Ala Ser Ser Pro Lys Pro
545                 550                 555                 560
```

```
Leu Pro Pro Pro Gly Ser Ser Leu Ser Cys Leu Gly His Val Gly
                565                 570                 575

Asp Arg Arg Leu Ser Ser Pro Trp Thr Pro Trp Pro Ala Ser Gly Ala
            580                 585                 590

Gly Pro Asp Ser Ser Ser Arg Val Ser Leu Leu Pro Pro Phe Leu Ser
            595                 600                 605

Asp Gln Ala Gln His Val His Ala Leu Gly Asn Phe Tyr Leu Phe Cys
            610                 615                 620

Gln Ala Thr Gly Pro Ala Asp Ile Arg Phe Val Trp Glu Lys Asn Gly
625                 630                 635                 640

Arg Ala Leu Glu Thr Cys Val Pro Val Gln Thr His Ala Leu Pro Asp
                645                 650                 655

Gly Arg Ala His Ala Leu Ser Trp Leu Gln Asp Ala Ile Arg Glu Ser
            660                 665                 670

Ala Glu Tyr Arg Cys Ser Val Leu Ser Ser Ala Gly Asn Lys Thr Ser
            675                 680                 685

Lys Val Gln Val Ala Val Met Arg Pro Glu Val Thr His Gln Glu Arg
            690                 695                 700

Trp Thr Arg Glu Leu Ser Ala Trp Arg Ala Val Ala Gly Glu His Asp
705                 710                 715                 720

Arg Met Met Gln Ser Trp Arg Lys Ala Trp Glu Ser Cys Ser Lys Asp
                725                 730                 735

Thr Leu

<210> SEQ ID NO 3
<211> LENGTH: 6408
<212> TYPE: DNA
<213> ORGANISM: Homo sapiens

<400> SEQUENCE: 3
atgcctgctc tgggcccagc tcttctccag gctctctggg ccgggtgggt cctcaccctc      60
cagccccttc accaactgca ttcactccc  aatggcacgt atctgcagca cctggcaagg     120
gaccccacct caggcaccct ctacctgggg gctaccaact tcctgttcca gctgagccct     180
gggctgcagc tggaggccac agtgtccacc ggccctgtgc tagacagcag ggactgcctg     240
ccacctgtga tgcctgatga gtgccccag  gcccagccta ccaacaaccc gaatcagctg     300
ctcctggtga gccaggggc  cctggtggta tgcgggagcg tgcaccaggg ggtctgtgaa     360
cagcggcgcc tggggcagct cgagcagctg ctgctgcggc cagagcggcc tggggacaca     420
caatatgtgg ctgccaatga tcctgcggtc agcacggtgg ggctggtagc ccagggcttg     480
gcaggggagc ccctcctgtt tgtggggcga ggatacacca gcaggggtgt gggggggtggc    540
attccaccca tcacaacccg ggccctgtgg ccgcccgacc ccaagctgc  cttctcctat     600
gaggagacag ccaagctggc agtgggccgc ctctccgagt acagccacca cttcgtgagt     660
gccttttgcac gtggggccag cgcctacttc ctgttcctgc ggcgggacct gcaggctcag    720
tctagagctt ttcgtgccta tgtatctcga gtgtgtctcc gggaccagca ctactactcc     780
tatgtggagt tgcctctggc ctgcgaaggt ggccgctacg gctgatcca ggctgcagct     840
gtggccacgt ccaggggagg tggcgcatgg gaggtgctct ttgcagcttt ctcctcggct     900
gcaccccca  ctgtgggccg gccccatcg  gcggctgctg gggcatctgg agcctctgcc     960
ctctgtgcct tcccctgga tgaggtggac cggcttgcta atcgcacgcg agatgcctgc    1020
tacacccggg agggtcgtgc tgaggatggg accgaggtgg cctacatcga gtatgatgtc    1080
```

```
aattctgact gtgcacagct gccagtggac accctggatg cttatccctg tggctcagac    1140
cacacgccca gccccatggc cagccgggtc ccgctggaag ccacaccaat tctggagtgg    1200
ccagggattc agctaacagc tgtggcagtc accatggaag atggacacac catcgctttc    1260
ctgggtgata gtcaagggca gctgcacagg gtctacttgg gcccagggag cgatggccac    1320
ccatactcca cacagagcat ccagcagggg tctgcagtga gcagagacct cacctttgat    1380
gggacctttg agcacctgta tgtcatgacc cagagcacac ttctgaaggt tcctgtggct    1440
tcctgtgctc agcacctgga ctgtgcatct tgccttgctc acagggaccc atactgtggg    1500
tggtgcgtgc tccttggcag gtgcagtcgc cgttctgagt gctcgagggg ccagggccca    1560
gagcagtggc tatggagctt ccagcctgag ctgggctgtc tgcaagtggc agccatgagt    1620
cctgccaaca tcagccgaga ggagacgagg gaggttttcc tatcagtgcc agacctgcca    1680
cccctgtggc caggggagtc atattcctgc cactttgggg aacatcagag tcctgccctg    1740
ctgactggtt ctggtgtgat gtgccnctcc ccagaccnta gtgaggcccc agtgctgccg    1800
agaggagccg actacgtatc cgtgagcgtg gagctcagat ttggcgctgt tgtgatcgcc    1860
aaaacttccc tctctttcta tgactgtgtg gcggtcactg aactccgccc atctgcgcag    1920
tgccaggcct gtgtgagcag ccgctggggg tgtaactggt gtgtctggca gcacctgtgc    1980
acccacaagg cctcgtgtga tgctgggccc atggttgcaa gccatcagag cccgcttgtc    2040
tccccagacc ctcctgcaag aggtggaccc agccctcc cacccacagc ccccaaagcc    2100
ctggccaccc ctgctcctga caccttccc gtggagcctg ggctccctc cacagccaca    2160 gcttcggaca tctcacctgg ggctagtcct tccctgctca gccctgggg gccatgggca    2220 ggttctggct ccatatcttc ccctggctcc acagggtcgc ctctccatga ggagccctcc    2280
cctcccagcc cccaaaatgg acctggaacc gctgtccctg cccccactga cttcagaccc    2340
tcagccacac ctgaggacct cttggcctcc ccgctgtcac cgtcagaggt agcagcagtg    2400 cccctgcag accctggccc cgaggctctt catcccacag tgcccctgga cctgccccct    2460
gccactgttc ctgccaccac tttcccaggg gccatgggct ccgtgaagcc cgccctggac    2520
tggctcacga gagaaggcgg cgagctgccc gaggcggacg agtggacggg gggtgacgca    2580
cccgccttct ccacttccac cctcctctca ggtgatggag actcagcaga gcttgagggc    2640
cctcccgccc ccctcatcct cccgtccagc ctcgactacc agtatgacac ccccgggctc    2700
tgggagctgg aagaggcgac cttggggca agctcctgcc cctgtgtgga gagcgttcag    2760
ggctccacgt tgatgccggt ccatgtggag cgggaaatcc ggctgctagg caggaacctg    2820 cacctttcc aggatggccc aggagacaat gagtgtgtga tggagctgga gggcctcgag    2880
gtggtggttg aggcccgggt cgagtgtgag ccacctccag atacccagtg ccatgtcacc    2940
tgccagcagc accagctcag ctatgaggct ctgcagccgg agctccgtgt ggggctgttt    3000
ctgcgtcggg ccgccgtct gcgtgtggac agtgctgagg ggctgcatgt ggtactgtat    3060
gactgttccg tgggacatgg agactgcagc cgctgccaaa ctgccatgcc ccagtatggc    3120
tgtgtgtggt gtgaggggga gcgtccacgt tgtgtgaccc gggaggcctg tggtgaggct    3180
gaggctgtgc ccacccagtg cccagcgccc ctcatccact cggtgagcc actgactggg    3240 cctgtagacg gaggcacccg tgtcaccatc aggggctcca acctgggcca gcatgtgcag    3300
gatgtgctgg gcatggtcac ggtggctgga gtgccctgtg ctgtgatgcc caggagtac    3360 gaggtctcca gcagcctcgt gtgcatcacc ggggccagtg ggaggaggt ggccggcgcc    3420
```

```
acagcggtgg aggtgccggg aagaggacgt ggtgtctcag aacacgactt tgcctaccag    3480
gatccgaagg tccattccat cttcccggcc cgcggcccca gagctggggg cacccgtctc    3540
accctgaatg gctccaagct cctgactggg cggctggagg acatccgagt ggtggttgga    3600
gaccagcctt gtcacttgct gccggagcag cagtcagaac aactgcggtg tgagaccagc    3660
ccacgcccca cgcctgccac gctccctgtg gctgtgtggt ttggggccac ggagcggagg    3720
cttcaacgcg gacagttcaa gtataccttg gaccccaaca tcacctctgc tggccccacc    3780
aagagcttcc tcagtggagg acgtgagata tgcgtccgtg gccagaatct ggacgtggta    3840
cagacgccaa gaatccgggt gaccgtggtc tcgagaatgc tgcagcccag ccaggggctt    3900
ggacggaggc gtcgcgtggt cccggagacg gcatgttccc ttggaccctc ctgcagtagc    3960
cagcaatttg aggagccgtg ccatgtcaac tcctcccagc tcatcacgtg ccgcacacct    4020
gccctcccag gcctgcctga ggaccctggg gtccgggtgg aatttatcct tgacaacctg    4080
gtctttgact ttgcaacact gaaccccaca ccttttctcct atgaggccga ccccaccctg    4140
cagccactca accctgagga ccccaccatg ccattccggc acaagcctgg gagtgtgttc    4200
tccgtggagg gggagaacct ggaccttgca atgtccaagg aggaggtggt ggctatgata    4260
ggggatggcc cctgtgtggt gaagacgctg acgcggcacc acctgtactg cgagcccccc    4320
gtggagcagc ccctgccacg gcaccatgcc ctccgagagg cacctgactc tttgcctgag    4380
ttcacggtgc agatggggaa cttgcgcttc tccctgggtc acgtgcagta tgacggcgag    4440
agccctgggg cttttcctgt ggcagcccag gtgggcttgg gggtgggcac ctctcttctg    4500
gctctgggtg tcatcatcat tgtcctcatg tacaggagga gagcaagca ggccctgagg    4560 gactataaga aggttcagat ccagctggag aatctggaga gcagtgtgcg ggaccgctgc    4620
aagaaggaat tcacagacct catgactgag atgaccgatc tcaccagtga cctcctgggc    4680
agcggcatcc ccttcctcga ctacaaggtg tatgcggaga ggatcttctt ccctgggcac    4740
cgcgagtcgc ccttgcaccg ggacctgggt gtgcctgaga cagacggcc cactgtggag    4800 caagggctgg ggcagctctc taacctgctc aacagcaagc tcttcctcac caagttcatc    4860
cacacgctgg agagccagcg caccttttca gctcgggacc gtgcctacgt ggcatctctg    4920
ctcaccgtgg cactgcatgg gaagcttgag tatttcactg acatcctccg cactctgctc    4980
agtgacctgg ttgcccagta tgtggccaag aaccccaagc tgatgctgcg caggacagag    5040
actgtggtgg agaagctgct caccaactgg atgtccatct gtctgtatac cttcgtgagg    5100
gactccgtag gggagcctct gtacatgctc tttcgaggga ttaagcacca agtggataag    5160
gggccagtgg acagtgtgac aggcaaggcc aaatacacct tgaacgacaa ccgcctgctc    5220
agagaggatg tggagtaccg tccccctgacc ttgaatgcac tattggctgt ggggcctggg    5280
gcaggagagg cccagggcgt gcccgtgaag gtcctagact gtgacaccat ctcccaggca    5340
aaggagaaga tgctggacca gctttataaa ggagtgcctc tcacccagcg gccagaccct    5400
cgcacccttg atgttgagtg gcggtctggg gtggccgggc acctcattct ttctgacgag    5460
gatgtcactt ctgaggtcca gggtctgtgg aggcgcctga acacactgca gcattacaag    5520
gtcccagatg gagcaactgt ggccctcgtc cctgcctcga ccaagcatgt gctccgggaa    5580
aaccaggatt atgtccctgg agagcggacc ccaatgctgg aggatgtaga tgaggggggc    5640
atccggccct ggcacctggt gaagccaagt gatgagccgg agccgccag gcctcggagg    5700 ggcagccttc ggggcgggga gcgtgagcgc gccaaggcca tccctgagat ctacctgacc    5760
cgcctgctgt ccatgaaggg caccctgcag aagttcgtgg atgacctgtt ccaggtgatt    5820
```

```
ctcagcacca gccgccccgt gccgctcgct gtgaagtact tctttgacct gctggatgag    5880
caggcccagc agcatggcat ctccgaccag gacaccatcc acatctggaa gaccaacagc    5940
ttgcctctga ggttctggat caatataata aaaaacccgc agtttgtgtt cgacgtgcaa    6000
acatctgata acatggatgc ggtgctcctt gtcattgcac agaccttcat ggacgcctgc    6060
accctggccg accacaagct gggccgggac tccccgatca acaaacttct gtatgcacgg    6120
gacattcccc ggtacaagcg gatggtggaa aggtactatg cagacatcag acagactgtc    6180
ccagccagcg accaagagat gaactctgtc ctggctgaac tgtcctggaa ctactccgga    6240
gacctcgggg cgcgagtggc cctgcatgaa ctctacaagt acatcaacaa gtactatgac    6300
cagatcatca ctgccctgga ggaggatggc acggcccaga gatgcagct gggctatcgg    6360 ctccagcaga ttgcagctgc tgtggaaaac aaggtcacag atctatag                 6408
```

<210> SEQ ID NO 4
<211> LENGTH: 2135
<212> TYPE: PRT
<213> ORGANISM: Homo sapiens

<400> SEQUENCE: 4

```
Met Pro Ala Leu Gly Pro Ala Leu Leu Gln Ala Leu Trp Ala Gly Trp
 1               5                  10                  15

Val Leu Thr Leu Gln Pro Leu Pro Pro Thr Ala Phe Thr Pro Asn Gly
             20                  25                  30

Thr Tyr Leu Gln His Leu Ala Arg Asp Pro Thr Ser Gly Thr Leu Tyr
         35                  40                  45

Leu Gly Ala Thr Asn Phe Leu Phe Gln Leu Ser Pro Gly Leu Gln Leu
     50                  55                  60

Glu Ala Thr Val Ser Thr Gly Pro Val Leu Asp Ser Arg Asp Cys Leu
 65                  70                  75                  80

Pro Pro Val Met Pro Asp Glu Cys Pro Gln Ala Gln Pro Thr Asn Asn
                 85                  90                  95

Pro Asn Gln Leu Leu Leu Val Ser Pro Gly Ala Leu Val Val Cys Gly
            100                 105                 110

Ser Val His Gln Gly Val Cys Glu Gln Arg Arg Leu Gly Gln Leu Glu
        115                 120                 125

Gln Leu Leu Leu Arg Pro Glu Arg Pro Gly Asp Thr Gln Tyr Val Ala
    130                 135                 140

Ala Asn Asp Pro Ala Val Ser Thr Val Gly Leu Val Ala Gln Gly Leu
145                 150                 155                 160

Ala Gly Glu Pro Leu Leu Phe Val Gly Arg Gly Tyr Thr Ser Arg Gly
                165                 170                 175

Val Gly Gly Gly Ile Pro Pro Ile Thr Thr Arg Ala Leu Trp Pro Pro
            180                 185                 190

Asp Pro Gln Ala Ala Phe Ser Tyr Glu Glu Thr Ala Lys Leu Ala Val
        195                 200                 205

Gly Arg Leu Ser Glu Tyr Ser His Phe Val Ser Ala Phe Ala Arg
    210                 215                 220

Gly Ala Ser Ala Tyr Phe Leu Phe Leu Arg Arg Asp Leu Gln Ala Gln
225                 230                 235                 240

Ser Arg Ala Phe Arg Ala Tyr Val Ser Arg Val Cys Leu Arg Asp Gln
                245                 250                 255

His Tyr Tyr Ser Tyr Val Glu Leu Pro Leu Ala Cys Glu Gly Gly Arg
            260                 265                 270
```

-continued

```
Tyr Gly Leu Ile Gln Ala Ala Val Ala Thr Ser Arg Glu Val Ala
        275                 280                 285
His Gly Glu Val Leu Phe Ala Ala Phe Ser Ser Ala Ala Pro Pro Thr
    290                 295                 300
Val Gly Arg Pro Pro Ser Ala Ala Gly Ala Ser Gly Ala Ser Ala
305                 310                 315                 320
Leu Cys Ala Phe Pro Leu Asp Glu Val Asp Arg Leu Ala Asn Arg Thr
                325                 330                 335
Arg Asp Ala Cys Tyr Thr Arg Glu Gly Arg Ala Glu Asp Gly Thr Glu
                340                 345                 350
Val Ala Tyr Ile Glu Tyr Asp Val Asn Ser Asp Cys Ala Gln Leu Pro
            355                 360                 365
Val Asp Thr Leu Asp Ala Tyr Pro Cys Gly Ser Asp His Thr Pro Ser
        370                 375                 380
Pro Met Ala Ser Arg Val Pro Leu Glu Ala Thr Pro Ile Leu Glu Trp
385                 390                 395                 400
Pro Gly Ile Gln Leu Thr Ala Val Ala Val Thr Met Glu Asp Gly His
                405                 410                 415
Thr Ile Ala Phe Leu Gly Asp Ser Gln Gly Gln Leu His Arg Val Tyr
            420                 425                 430
Leu Gly Pro Gly Ser Asp Gly His Pro Tyr Ser Thr Gln Ser Ile Gln
        435                 440                 445
Gln Gly Ser Ala Val Ser Arg Asp Leu Thr Phe Asp Gly Thr Phe Glu
    450                 455                 460
His Leu Tyr Val Met Thr Gln Ser Thr Leu Leu Lys Val Pro Val Ala
465                 470                 475                 480
Ser Cys Ala Gln His Leu Asp Cys Ala Ser Cys Leu Ala His Arg Asp
                485                 490                 495
Pro Tyr Cys Gly Trp Cys Val Leu Leu Gly Arg Cys Ser Arg Arg Ser
            500                 505                 510
Glu Cys Ser Arg Gly Gln Gly Pro Glu Gln Trp Leu Trp Ser Phe Gln
        515                 520                 525
Pro Glu Leu Gly Cys Leu Gln Val Ala Ala Met Ser Pro Ala Asn Ile
    530                 535                 540
Ser Arg Glu Glu Thr Arg Glu Val Phe Leu Ser Val Pro Asp Leu Pro
545                 550                 555                 560
Pro Leu Trp Pro Gly Glu Ser Tyr Ser Cys His Phe Gly Glu His Gln
                565                 570                 575
Ser Pro Ala Leu Leu Thr Gly Ser Gly Val Met Cys Pro Ser Pro Asp
            580                 585                 590
Pro Ser Glu Ala Pro Val Leu Pro Arg Gly Ala Asp Tyr Val Ser Val
        595                 600                 605
Ser Val Glu Leu Arg Phe Gly Ala Val Val Ile Ala Lys Thr Ser Leu
    610                 615                 620
Ser Phe Tyr Asp Cys Val Ala Val Thr Glu Leu Arg Pro Ser Ala Gln
625                 630                 635                 640
Cys Gln Ala Cys Val Ser Ser Arg Trp Gly Cys Asn Trp Cys Val Trp
                645                 650                 655
Gln His Leu Cys Thr His Lys Ala Ser Cys Asp Ala Gly Pro Met Val
            660                 665                 670
Ala Ser His Gln Ser Pro Leu Val Ser Pro Asp Pro Pro Ala Arg Gly
        675                 680                 685
```

```
Gly Pro Ser Pro Ser Pro Pro Thr Ala Pro Lys Ala Leu Ala Thr Pro
690                 695                 700

Ala Pro Asp Thr Leu Pro Val Glu Pro Gly Ala Pro Ser Thr Ala Thr
705                 710                 715                 720

Ala Ser Asp Ile Ser Pro Gly Ala Ser Pro Ser Leu Leu Ser Pro Trp
            725                 730                 735

Gly Pro Trp Ala Gly Ser Gly Ile Ser Ser Pro Gly Ser Thr Gly
                740                 745                 750

Ser Pro Leu His Glu Glu Pro Ser Pro Ser Pro Gln Asn Gly Pro
            755                 760                 765

Gly Thr Ala Val Pro Ala Pro Thr Asp Phe Arg Pro Ser Ala Thr Pro
770                 775                 780

Glu Asp Leu Leu Ala Ser Pro Leu Ser Pro Ser Glu Val Ala Ala Val
785                 790                 795                 800

Pro Pro Ala Asp Pro Gly Pro Glu Ala Leu His Pro Thr Val Pro Leu
                805                 810                 815

Asp Leu Pro Pro Ala Thr Val Pro Ala Thr Thr Phe Pro Gly Ala Met
                820                 825                 830

Gly Ser Val Lys Pro Ala Leu Asp Trp Leu Thr Arg Glu Gly Gly Glu
            835                 840                 845

Leu Pro Glu Ala Asp Glu Trp Thr Gly Gly Asp Ala Pro Ala Phe Ser
850                 855                 860

Thr Ser Thr Leu Leu Ser Gly Asp Gly Asp Ser Ala Glu Leu Glu Gly
865                 870                 875                 880

Pro Pro Ala Pro Leu Ile Leu Pro Ser Ser Leu Asp Tyr Gln Tyr Asp
            885                 890                 895

Thr Pro Gly Leu Trp Glu Leu Glu Ala Thr Leu Gly Ala Ser Ser
            900                 905                 910

Cys Pro Cys Val Glu Ser Val Gln Gly Ser Thr Leu Met Pro Val His
            915                 920                 925

Val Glu Arg Glu Ile Arg Leu Leu Gly Arg Asn Leu His Leu Phe Gln
930                 935                 940

Asp Gly Pro Gly Asp Asn Glu Cys Val Met Glu Leu Glu Gly Leu Glu
945                 950                 955                 960

Val Val Val Glu Ala Arg Val Glu Cys Glu Pro Pro Asp Thr Gln
                965                 970                 975

Cys His Val Thr Cys Gln Gln His Gln Leu Ser Tyr Glu Ala Leu Gln
            980                 985                 990

Pro Glu Leu Arg Val Gly Leu Phe  Leu Arg Arg Ala Gly  Arg Leu Arg
            995                 1000                1005

Val Asp  Ser Ala Glu Gly Leu  His Val Val Leu Tyr  Asp Cys Ser
    1010                1015                1020

Val Gly  His Gly Asp Cys Ser  Arg Cys Gln Thr Ala  Met Pro Gln
    1025                1030                1035

Tyr Gly  Cys Val Trp Cys Glu  Gly Glu Arg Pro Arg  Cys Val Thr
    1040                1045                1050

Arg Glu  Ala Cys Gly Glu Ala  Glu Ala Val Ala Thr  Gln Cys Pro
    1055                1060                1065

Ala Pro  Leu Ile His Ser Val  Glu Pro Leu Thr Gly  Pro Val Asp
    1070                1075                1080

Gly Gly  Thr Arg Val Thr Ile  Arg Gly Ser Asn Leu  Gly Gln His
    1085                1090                1095

Val Gln  Asp Val Leu Gly Met  Val Thr Val Ala Gly  Val Pro Cys
```

-continued

```
                1100                1105                1110
Ala Val Asp Ala Gln Glu Tyr Glu Val Ser Ser Leu Val Cys
    1115                1120                1125
Ile Thr Gly Ala Ser Gly Glu Glu Val Ala Gly Thr Ala Val
    1130                1135                1140
Glu Val Pro Gly Arg Gly Gly Val Ser Glu His Asp Phe Ala
    1145                1150                1155
Tyr Gln Asp Pro Lys Val His Ser Ile Phe Pro Ala Arg Gly Pro
    1160                1165                1170
Arg Ala Gly Gly Thr Arg Leu Thr Leu Asn Gly Ser Lys Leu Leu
    1175                1180                1185
Thr Gly Arg Leu Glu Asp Ile Arg Val Val Gly Asp Gln Pro
    1190                1195                1200
Cys His Leu Leu Pro Glu Gln Gln Ser Glu Gln Leu Arg Cys Glu
    1205                1210                1215
Thr Ser Pro Arg Pro Thr Pro Ala Thr Leu Pro Val Ala Val Trp
    1220                1225                1230
Phe Gly Ala Thr Glu Arg Arg Leu Gln Arg Gly Gln Phe Lys Tyr
    1235                1240                1245
Thr Leu Asp Pro Asn Ile Thr Ser Ala Gly Pro Thr Lys Ser Phe
    1250                1255                1260
Leu Ser Gly Gly Arg Glu Ile Cys Val Arg Gly Gln Asn Leu Asp
    1265                1270                1275
Val Val Gln Thr Pro Arg Ile Arg Val Thr Val Val Ser Arg Met
    1280                1285                1290
Leu Gln Pro Ser Gln Gly Leu Gly Arg Arg Arg Val Val Pro
    1295                1300                1305
Glu Thr Ala Cys Ser Leu Gly Pro Ser Cys Ser Ser Gln Gln Phe
    1310                1315                1320
Glu Glu Pro Cys His Val Asn Ser Ser Gln Leu Ile Thr Cys Arg
    1325                1330                1335
Thr Pro Ala Leu Pro Gly Leu Pro Glu Asp Pro Trp Val Arg Val
    1340                1345                1350
Glu Phe Ile Leu Asp Asn Leu Val Phe Asp Phe Ala Thr Leu Asn
    1355                1360                1365
Pro Thr Pro Phe Ser Tyr Glu Ala Asp Pro Thr Leu Gln Pro Leu
    1370                1375                1380
Asn Pro Glu Asp Pro Thr Met Pro Phe Arg His Lys Pro Gly Ser
    1385                1390                1395
Val Phe Ser Val Glu Gly Glu Asn Leu Asp Leu Ala Met Ser Lys
    1400                1405                1410
Glu Glu Val Val Ala Met Ile Gly Asp Gly Pro Cys Val Val Lys
    1415                1420                1425
Thr Leu Thr Arg His His Leu Tyr Cys Glu Pro Pro Val Glu Gln
    1430                1435                1440
Pro Leu Pro Arg His His Ala Leu Arg Glu Ala Pro Asp Ser Leu
    1445                1450                1455
Pro Glu Phe Thr Val Gln Met Gly Asn Leu Arg Phe Ser Leu Gly
    1460                1465                1470
His Val Gln Tyr Asp Gly Glu Ser Pro Gly Ala Phe Pro Val Ala
    1475                1480                1485
Ala Gln Val Gly Leu Gly Val Gly Thr Ser Leu Leu Ala Leu Gly
    1490                1495                1500
```

```
Val Ile Ile Ile Val Leu Met Tyr Arg Arg Lys Ser Lys Gln Ala
1505                1510                1515

Leu Arg Asp Tyr Lys Lys Val Gln Ile Gln Leu Glu Asn Leu Glu
1520                1525                1530

Ser Ser Val Arg Asp Arg Cys Lys Lys Glu Phe Thr Asp Leu Met
1535                1540                1545

Thr Glu Met Thr Asp Leu Thr Ser Asp Leu Leu Gly Ser Gly Ile
1550                1555                1560

Pro Phe Leu Asp Tyr Lys Val Tyr Ala Glu Arg Ile Phe Phe Pro
1565                1570                1575

Gly His Arg Glu Ser Pro Leu His Arg Asp Leu Gly Val Pro Glu
1580                1585                1590

Ser Arg Arg Pro Thr Val Glu Gln Gly Leu Gly Gln Leu Ser Asn
1595                1600                1605

Leu Leu Asn Ser Lys Leu Phe Leu Thr Lys Phe Ile His Thr Leu
1610                1615                1620

Glu Ser Gln Arg Thr Phe Ser Ala Arg Asp Arg Ala Tyr Val Ala
1625                1630                1635

Ser Leu Leu Thr Val Ala Leu His Gly Lys Leu Glu Tyr Phe Thr
1640                1645                1650

Asp Ile Leu Arg Thr Leu Leu Ser Asp Leu Val Ala Gln Tyr Val
1655                1660                1665

Ala Lys Asn Pro Lys Leu Met Leu Arg Arg Thr Glu Thr Val Val
1670                1675                1680

Glu Lys Leu Leu Thr Asn Trp Met Ser Ile Cys Leu Tyr Thr Phe
1685                1690                1695

Val Arg Asp Ser Val Gly Glu Pro Leu Tyr Met Leu Phe Arg Gly
1700                1705                1710

Ile Lys His Gln Val Asp Lys Gly Pro Val Asp Ser Val Thr Gly
1715                1720                1725

Lys Ala Lys Tyr Thr Leu Asn Asp Asn Arg Leu Leu Arg Glu Asp
1730                1735                1740

Val Glu Tyr Arg Pro Leu Thr Leu Asn Ala Leu Leu Ala Val Gly
1745                1750                1755

Pro Gly Ala Gly Glu Ala Gln Gly Val Pro Val Lys Val Leu Asp
1760                1765                1770

Cys Asp Thr Ile Ser Gln Ala Lys Glu Lys Met Leu Asp Gln Leu
1775                1780                1785

Tyr Lys Gly Val Pro Leu Thr Gln Arg Pro Asp Pro Arg Thr Leu
1790                1795                1800

Asp Val Glu Trp Arg Ser Gly Val Ala Gly His Leu Ile Leu Ser
1805                1810                1815

Asp Glu Asp Val Thr Ser Glu Val Gln Gly Leu Trp Arg Arg Leu
1820                1825                1830

Asn Thr Leu Gln His Tyr Lys Val Pro Asp Gly Ala Thr Val Ala
1835                1840                1845

Leu Val Pro Cys Leu Thr Lys His Val Leu Arg Glu Asn Gln Asp
1850                1855                1860

Tyr Val Pro Gly Glu Arg Thr Pro Met Leu Glu Asp Val Asp Glu
1865                1870                1875

Gly Gly Ile Arg Pro Trp His Leu Val Lys Pro Ser Asp Glu Pro
1880                1885                1890
```

Glu Pro Pro Arg Pro Arg Arg Gly Ser Leu Arg Gly Gly Glu Arg
    1895                1900                1905

Glu Arg Ala Lys Ala Ile Pro Glu Ile Tyr Leu Thr Arg Leu Leu
    1910                1915                1920

Ser Met Lys Gly Thr Leu Gln Lys Phe Val Asp Leu Phe Gln
    1925                1930                1935

Val Ile Leu Ser Thr Ser Arg Pro Val Pro Leu Ala Val Lys Tyr
    1940                1945                1950

Phe Phe Asp Leu Leu Asp Glu Gln Ala Gln Gln His Gly Ile Ser
    1955                1960                1965

Asp Gln Asp Thr Ile His Ile Trp Lys Thr Asn Ser Leu Pro Leu
    1970                1975                1980

Arg Phe Trp Ile Asn Ile Ile Lys Asn Pro Gln Phe Val Phe Asp
    1985                1990                1995

Val Gln Thr Ser Asp Asn Met Asp Ala Val Leu Leu Val Ile Ala
    2000                2005                2010

Gln Thr Phe Met Asp Ala Cys Thr Leu Ala Asp His Lys Leu Gly
    2015                2020                2025

Arg Asp Ser Pro Ile Asn Lys Leu Leu Tyr Ala Arg Asp Ile Pro
    2030                2035                2040

Arg Tyr Lys Arg Met Val Glu Arg Tyr Tyr Ala Asp Ile Arg Gln
    2045                2050                2055

Thr Val Pro Ala Ser Asp Gln Glu Met Asn Ser Val Leu Ala Glu
    2060                2065                2070

Leu Ser Trp Asn Tyr Ser Gly Asp Leu Gly Ala Arg Val Ala Leu
    2075                2080                2085

His Glu Leu Tyr Lys Tyr Ile Asn Lys Tyr Tyr Asp Gln Ile Ile
    2090                2095                2100

Thr Ala Leu Glu Glu Asp Gly Thr Ala Gln Lys Met Gln Leu Gly
    2105                2110                2115

Tyr Arg Leu Gln Gln Ile Ala Ala Ala Val Glu Asn Lys Val Thr
    2120                2125                2130

Asp Leu
    2135

<210> SEQ ID NO 5
<211> LENGTH: 20
<212> TYPE: DNA
<213> ORGANISM: Artificial
<220> FEATURE:
<223> OTHER INFORMATION: Plxnb1 sense

<400> SEQUENCE: 5
tgggtcatgt gcagtacgat                                               20

<210> SEQ ID NO 6
<211> LENGTH: 20
<212> TYPE: DNA
<213> ORGANISM: Artificial
<220> FEATURE:
<223> OTHER INFORMATION: Plxnb1 antisense

<400> SEQUENCE: 6
cactgctctc caggttctcc                                               20

<210> SEQ ID NO 7
<211> LENGTH: 20
<212> TYPE: DNA

```
<213> ORGANISM: Artificial
<220> FEATURE:
<223> OTHER INFORMATION: Plxnb2 sense

<400> SEQUENCE: 7
aggggagcct ctctacaagc                                               20

<210> SEQ ID NO 8
<211> LENGTH: 20
<212> TYPE: DNA
<213> ORGANISM: Artificial
<220> FEATURE:
<223> OTHER INFORMATION: Plxnb2 antisense

<400> SEQUENCE: 8
tcgatccctt catcctgaac                                               20

<210> SEQ ID NO 9
<211> LENGTH: 20
<212> TYPE: DNA
<213> ORGANISM: Artificial
<220> FEATURE:
<223> OTHER INFORMATION: Plxnb3 sense

<400> SEQUENCE: 9
atatgctgag cgtgccttct                                               20

<210> SEQ ID NO 10
<211> LENGTH: 20
<212> TYPE: DNA
<213> ORGANISM: Artificial
<220> FEATURE:
<223> OTHER INFORMATION: Plxnb3 antisense

<400> SEQUENCE: 10
tgctgttgag caaattggag                                               20

<210> SEQ ID NO 11
<211> LENGTH: 20
<212> TYPE: DNA
<213> ORGANISM: Artificial
<220> FEATURE:
<223> OTHER INFORMATION: CD72 sense

<400> SEQUENCE: 11
gccttctcct gtcctgtctg                                               20

<210> SEQ ID NO 12
<211> LENGTH: 20
<212> TYPE: DNA
<213> ORGANISM: Artificial
<220> FEATURE:
<223> OTHER INFORMATION: CD72 antisense

<400> SEQUENCE: 12
cctcctggaa ctgctgagac                                               20

<210> SEQ ID NO 13
<211> LENGTH: 20
<212> TYPE: DNA
<213> ORGANISM: Artificial
<220> FEATURE:
<223> OTHER INFORMATION: Alpl sense

<400> SEQUENCE: 13
aacccagaca caagcattcc                                               20
```

<210> SEQ ID NO 14
<211> LENGTH: 20
<212> TYPE: DNA
<213> ORGANISM: Artificial
<220> FEATURE:
<223> OTHER INFORMATION: Alpl antisense

<400> SEQUENCE: 14
gcctttgagg tttttggtca                                         20

<210> SEQ ID NO 15
<211> LENGTH: 20
<212> TYPE: DNA
<213> ORGANISM: Artificial
<220> FEATURE:
<223> OTHER INFORMATION: Bglap sense

<400> SEQUENCE: 15
gcgctctgtc tctctgacct                                         20

<210> SEQ ID NO 16
<211> LENGTH: 20
<212> TYPE: DNA
<213> ORGANISM: Artificial
<220> FEATURE:
<223> OTHER INFORMATION: Bglap antisense

<400> SEQUENCE: 16
accttattgc cctcctgctt                                         20

<210> SEQ ID NO 17
<211> LENGTH: 20
<212> TYPE: DNA
<213> ORGANISM: Artificial
<220> FEATURE:
<223> OTHER INFORMATION: Col1a1 sense

<400> SEQUENCE: 17
gagcggagag tactggatcg                                         20

<210> SEQ ID NO 18
<211> LENGTH: 20
<212> TYPE: DNA
<213> ORGANISM: Artificial
<220> FEATURE:
<223> OTHER INFORMATION: Col1a1 antisense

<400> SEQUENCE: 18
gttcgggctg atgtaccagt                                         20

<210> SEQ ID NO 19
<211> LENGTH: 20
<212> TYPE: DNA
<213> ORGANISM: Artificial
<220> FEATURE:
<223> OTHER INFORMATION: Gapdh sense

<400> SEQUENCE: 19
acccagaaga ctgtggatgg                                         20

<210> SEQ ID NO 20
<211> LENGTH: 20
<212> TYPE: DNA
<213> ORGANISM: Artificial
<220> FEATURE:

```
<223> OTHER INFORMATION: Gapdh antisense

<400> SEQUENCE: 20
cacattgggg gtaggaacac                                              20
```